US007806907B2

(12) United States Patent
Banbury et al.

(10) Patent No.: US 7,806,907 B2
(45) Date of Patent: Oct. 5, 2010

(54) SKIN LESION EXCISER AND SKIN-CLOSURE DEVICE THEREFOR

(75) Inventors: Michael K. Banbury, Cleveland Heights, OH (US); Jillian E. Banbury, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1826 days.

(21) Appl. No.: 10/261,155

(22) Filed: Sep. 30, 2002

(65) Prior Publication Data

US 2003/0078596 A1  Apr. 24, 2003

Related U.S. Application Data

(60) Provisional application No. 60/326,254, filed on Oct. 1, 2001, provisional application No. 60/332,276, filed on Nov. 14, 2001, provisional application No. 60/357,520, filed on Feb. 15, 2002.

(51) Int. Cl.
  *A61B 17/32* (2006.01)
(52) U.S. Cl. ...................... 606/167; 606/213
(58) Field of Classification Search ............... 606/110, 606/120, 167, 170, 166, 213; 600/564
  See application file for complete search history.

(56) References Cited

U.S. PATENT DOCUMENTS

| 363,538 | A |  | 5/1887 | Penny |  |
|---|---|---|---|---|---|
| 2,156,351 | A | * | 5/1939 | Paul | 40/324 |
| 2,994,321 | A |  | 8/1961 | Tischler | 128/2 |
| 3,323,208 | A |  | 6/1967 | Hurley, Jr. |  |
| 3,353,531 | A |  | 11/1967 | Armao | 128/2 |
| 3,373,742 | A |  | 3/1968 | Shears et al. | 128/171 |
| 3,391,690 | A |  | 7/1968 | Armao | 128/2 |
| 3,520,306 | A |  | 7/1970 | Gardner et al. | 128/335 |
| 3,707,970 | A |  | 1/1973 | Smirnov et al. |  |

(Continued)

FOREIGN PATENT DOCUMENTS

DE  3111996  10/1982

(Continued)

*Primary Examiner*—Anhtuan T Nguyen
*Assistant Examiner*—Tuan V Nguyen
(74) *Attorney, Agent, or Firm*—Wood, Herron & Evans, L.L.P.

(57) ABSTRACT

A skin lesion exciser including a moving blade, wherein excision of a skin lesion placed in proximity to the blade is effected by movement of the blade against the skin, a moving engagement portion, wherein the blade and the engagement portion have coincident movement, and a skin-closure device having an open condition prior to excision of the skin lesion, and a closed condition in which the device holds the skin closed after excision of the skin lesion. The device is in engagement with the engagement portion during movement of the blade, and the device is moved from its open to its closed condition in response to movement of the engagement portion. The excision of the skin lesion and the closure of the skin are substantially simultaneous. The present invention also provides a method for excising a skin lesion including: positioning a skin lesion above a moving blade; slicing the lesion from the skin with the blade; and substantially simultaneously with excision of the lesion, closing the skin beneath the moving blade. The present invention also provides a skin-closure device which may be used in conjunction with an inventive exciser.

4 Claims, 19 Drawing Sheets

U.S. PATENT DOCUMENTS

| | | | |
|---|---|---|---|
| 3,857,140 A | 12/1974 | Leveen | 24/87 TB |
| 4,399,810 A | 8/1983 | Samuels et al. | |
| 4,465,071 A | 8/1984 | Samuels et al. | |
| 4,467,805 A | 8/1984 | Fukuda | |
| 4,610,251 A | 9/1986 | Kumar | |
| 4,651,753 A | 3/1987 | Lifton | |
| 4,682,598 A * | 7/1987 | Beraha | 606/142 |
| 4,754,756 A | 7/1988 | Shelanski | |
| 4,815,468 A | 3/1989 | Annand | 128/335 |
| 4,943,295 A | 7/1990 | Hartlaub et al. | 606/131 |
| 4,950,284 A | 8/1990 | Green et al. | |
| 4,976,909 A | 12/1990 | Dorband et al. | |
| 5,099,827 A | 3/1992 | Melzer et al. | |
| 5,104,394 A * | 4/1992 | Knoepfler | 606/143 |
| 5,127,915 A * | 7/1992 | Mattson | 606/120 |
| 5,176,703 A | 1/1993 | Peterson | 606/216 |
| 5,190,560 A | 3/1993 | Woods et al. | |
| 5,209,755 A | 5/1993 | Abrahan et al. | |
| 5,212,879 A | 5/1993 | Biro et al. | |
| 5,213,907 A | 5/1993 | Caballero | 428/678 |
| 5,219,354 A | 6/1993 | Choudhury et al. | |
| 5,258,012 A | 11/1993 | Luscombe et al. | 606/220 |
| 5,358,510 A | 10/1994 | Luscombe et al. | 606/220 |
| 5,423,857 A | 6/1995 | Rosenman et al. | 606/219 |
| 5,425,740 A | 6/1995 | Hutchinson, Jr. | |
| 5,425,741 A | 6/1995 | Lemp et al. | |
| 5,527,319 A * | 6/1996 | Green et al. | 606/143 |
| 5,555,892 A | 9/1996 | Tipton | |
| 5,588,967 A | 12/1996 | Lemp et al. | |
| 5,609,600 A | 3/1997 | Love et al. | |
| 5,620,452 A * | 4/1997 | Yoon | 606/151 |
| 5,624,451 A | 4/1997 | Segal | |
| 5,628,759 A | 5/1997 | McCool et al. | |
| 5,674,234 A | 10/1997 | McCool et al. | |
| 5,868,763 A | 2/1999 | Spence et al. | |
| 5,931,847 A | 8/1999 | Bittner et al. | |
| 5,993,399 A | 11/1999 | Pruitt et al. | |
| 6,015,417 A | 1/2000 | Reynolds, Jr. | |
| 6,106,542 A * | 8/2000 | Toybin et al. | 606/205 |
| 6,126,615 A | 10/2000 | Allen et al. | 600/562 |
| 6,146,399 A | 11/2000 | Lee | |
| 6,319,474 B1 | 11/2001 | Krulevitch et al. | |
| 6,638,235 B2 | 10/2003 | Miller et al. | |
| 6,719,777 B2 | 4/2004 | Ginn et al. | |
| 6,758,824 B1 | 7/2004 | Miller et al. | |
| 6,811,555 B1 | 11/2004 | Willis et al. | |
| 2004/0009289 A1 | 1/2004 | Carley et al. | |
| 2004/0010285 A1 | 1/2004 | Carley et al. | |
| 2004/0039414 A1 | 2/2004 | Carley et al. | |
| 2004/0073236 A1 | 4/2004 | Carley et al. | |

FOREIGN PATENT DOCUMENTS

| | | |
|---|---|---|
| EP | 0092383 | 10/1983 |
| EP | 0 622 046 A2 | 11/1994 |
| WO | WO95/34245 | 12/1995 |
| WO | WO 00/56227 A1 | 9/2000 |
| WO | W 03/028563 A2 | 4/2003 |

* cited by examiner

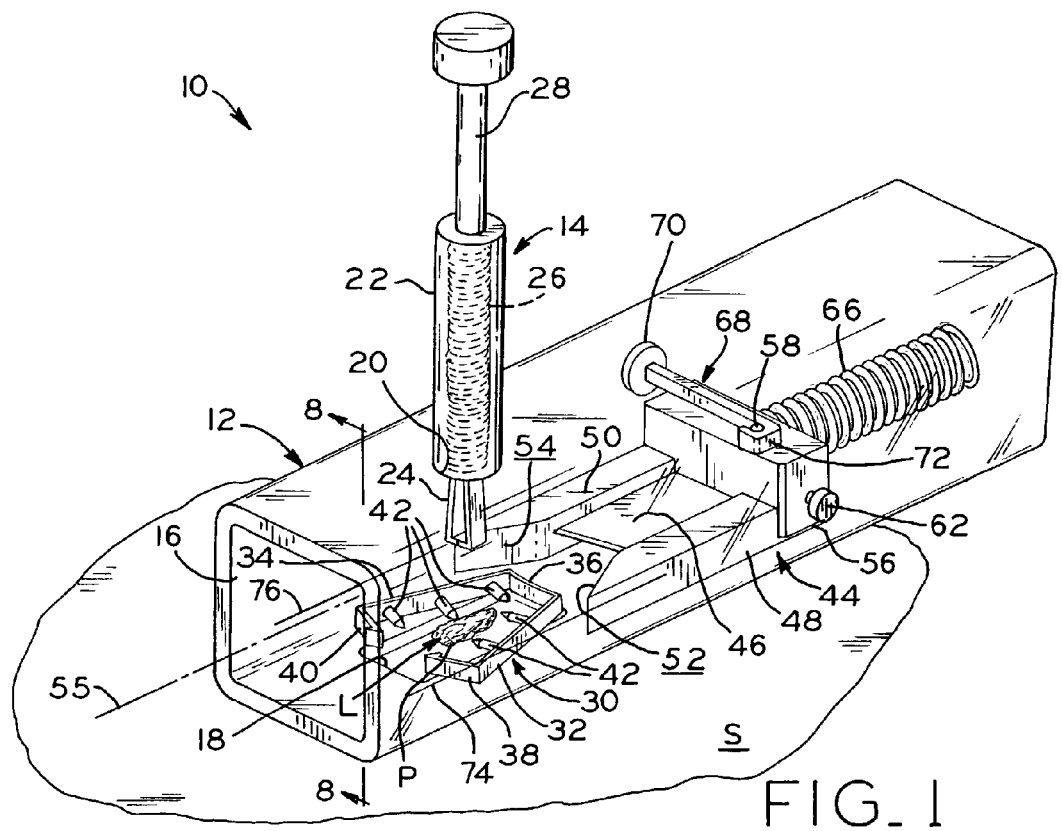
FIG_1
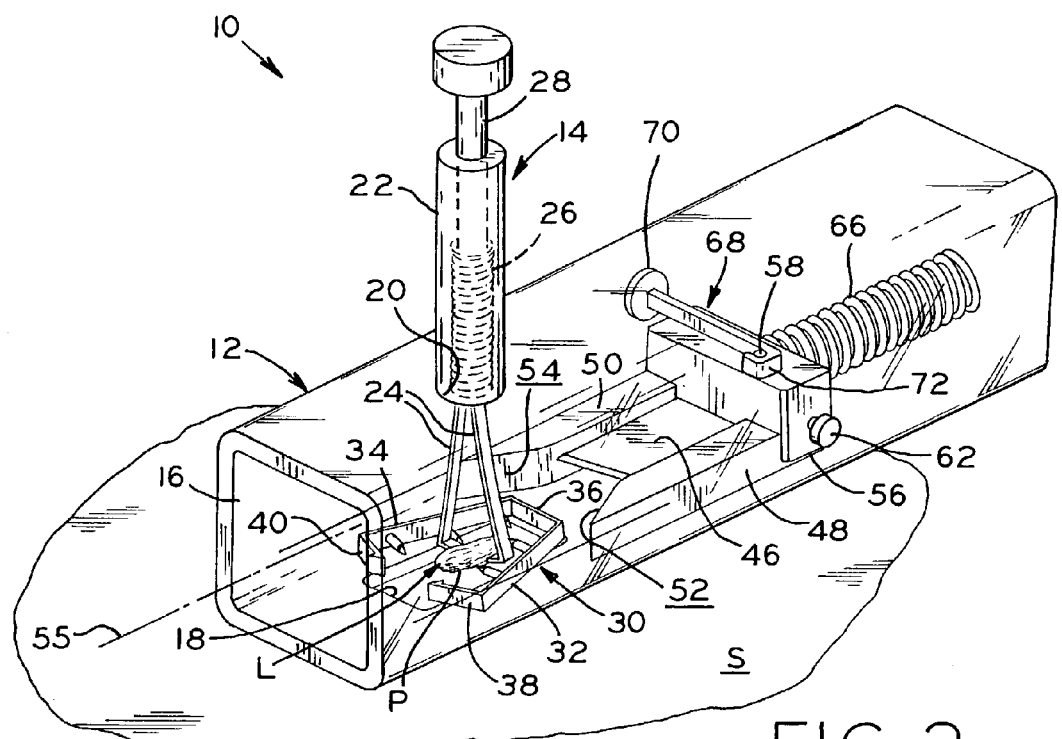
FIG_2

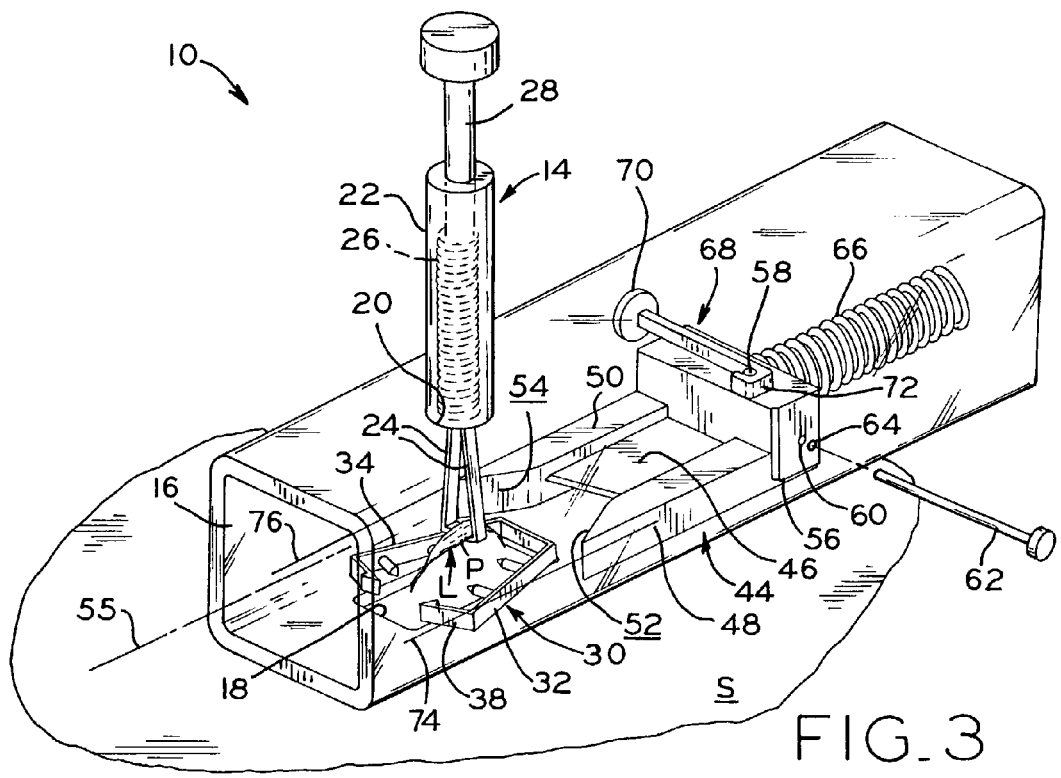
FIG_3
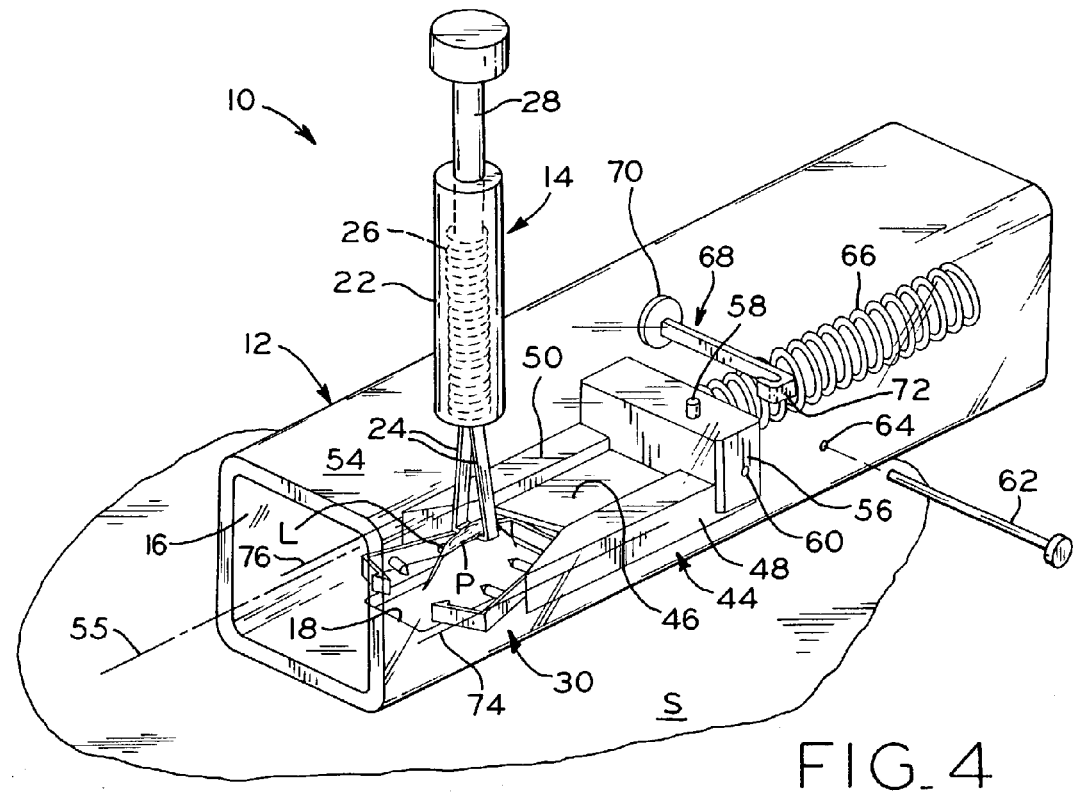
FIG_4

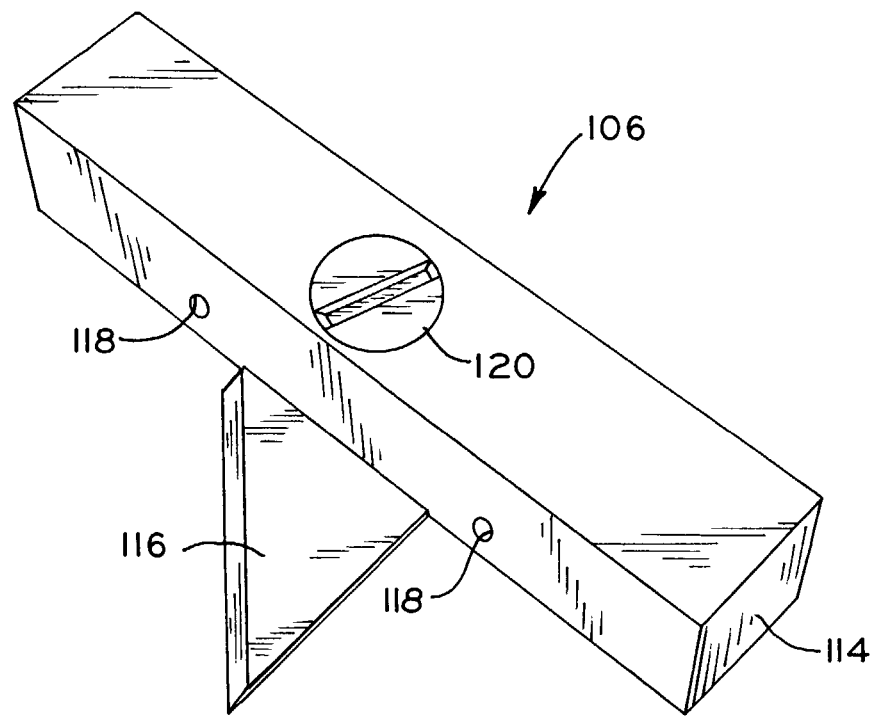
FIG_13
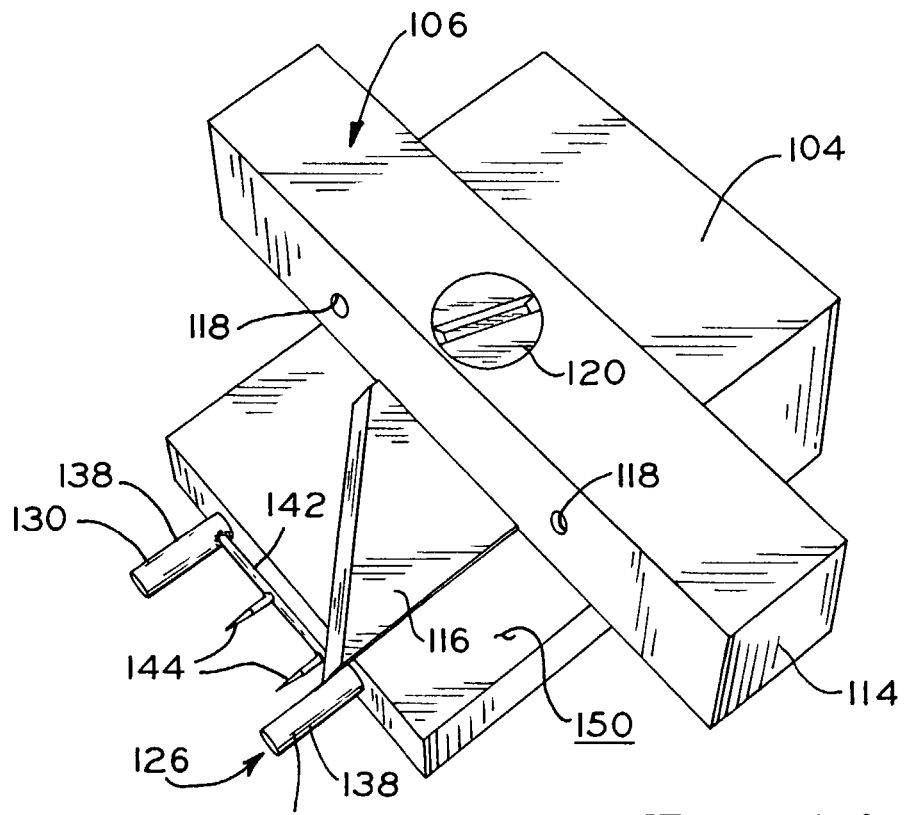
FIG_14

FIG_16

FIG._21

SKIN LESION EXCISER AND SKIN-CLOSURE DEVICE THEREFOR

CROSS REFERENCE TO RELATED APPLICATIONS

This application is related to and claims the benefit under 35 U.S.C. §119(e) of U.S. Provisional Applications No. 60/326,254 filed Oct. 1, 2001, No. 60/332,276 filed Nov. 14, 2001, and No. 60/357,520 filed Feb. 15, 2002.

BACKGROUND OF THE INVENTION

1. Field of Invention

The present invention relates to the excision of skin tags, moles, lesions and other types of discrete patches or points on the skin (herein collectively referred to as lesions) from a human or animal.

2. Description of the Related Art

In 1996, the Center for Disease Control estimated that approximately 2 million skin lesions were excised (from humans) per year in the United States. This estimate was based on voluntary reporting by several centers and is most likely an underestimate of the actual number of skin lesions excised. In that same year, it was estimated that approximately 8 million skin lesions were excised (again, from humans) per year in industrialized nations worldwide.

The current medical practice model for treatment of skin cancer involves preliminary screening of skin lesions. This requires surgical excision of the skin lesion typically done in the office of a plastic surgeon. Alternative methods by which dermatologists can biopsy lesions in screening for cancer include shaving small segments for microscopic analysis, or punch biopsy. A punch biopsy involves coring out a small sample of the skin lesion and then leaving the skin defect open with a covering bandage. Because it is such a small sample, no skin closure is used.

When an individual identifies a mole or skin lesion that he or she wishes excised, either for cosmetic purposes or screening for skin cancer, the first approach is often a visit to the family practice physician or internist. At that time, evaluation of the lesion is performed and if necessary, referral to the dermatologist or plastic surgeon is given.

Plastic surgeons or other physicians performing surgical excision typically prepare and drape the area, inject the area locally with an anesthetic such as lidocaine, and then perform a surgical excision using a scalpel. The skin is re-approximated and closed using suture material, which is sewn and then tied.

These methods of skin lesion excision can be awkward, time consuming and inconvenient. Often patients fail to follow up with screening for skin lesions because of the inconvenience and fear of surgical procedures even though minor. A device and/or method of simply and effectively excising skin lesions while the underlying skin is simultaneously re-approximated and closed is highly desirable. Patients would then be more likely to follow through with the procedures and derive greater satisfaction overall. This would also lead to earlier detection of skin cancer when it is more easily treated.

SUMMARY OF THE INVENTION

In accordance with the present invention, devices and methods are provided by which skin lesions are excised safely and effectively with substantially simultaneous closure of the skin. The excision and closure of the excision site through use of the present invention could change the paradigm for screening and treatment of skin cancer in the industrialized world.

The inventive devices are quick and easy to manipulate, and the method requires only a minimum of local anesthesia or analgesia for patient comfort. The inventive methods could be performed in the office of the internist or family practice physician where the patient initially presents and often by a physician extender, such as a nurse practitioner, under the supervision and guidance of the physician.

Through use of the present invention, it would be unnecessary for patients to make a secondary appointment with another physician for examination and potential excision of the lesion. The usual 30-minute procedure could be reduced to 2 or 3 minutes using the present invention. Moreover, the excised lesion may be easily retrieved from the inventive device and submitted for pathologic examination.

The present invention provides a skin lesion exciser including a moving blade, wherein excision of a skin lesion placed in proximity to the blade is effected by movement of the blade against the skin, a moving engagement portion, wherein the blade and the engagement portion have coincident movement, and a skin-closure device having an open condition prior to excision of the skin lesion, and a closed condition in which the device holds the skin closed after excision of the skin lesion. The device is in engagement with the engagement portion during movement of the blade, and the device is moved from its open to its closed condition in response to movement of the engagement portion. The excision of the skin lesion and the closure of the skin are substantially simultaneous.

The present invention also provides a method for excising a skin lesion including: positioning a skin lesion above a moving blade; slicing the lesion from the skin with the blade; and substantially simultaneously with excision of the lesion, closing the skin beneath the moving blade.

The present invention also provides a skin lesion exciser including relatively moving first and second members, a moving blade attached to at least one of the first and second members, excision of a skin lesion placed in proximity to the blade being effected by movement of the blade against the skin, a skin-closure device having first and second halves, each device half connected to a respective first and second member. The device has an open condition prior to excision of the skin lesion, and movement of the first and second members bring the device halves into engagement. In engagement, the device halves have a closed condition in which skin surrounding the perimeter of the lesion to be excised is pinched between the device halves and the device holds the skin closed after excision of the skin lesion, and movement of the blade against the skin occurs in the device closed condition.

The present invention also provides a method for excising a skin lesion including: positioning a skin lesion above a moving blade; engaging two halves of a skin-closure device and pinching skin located outside the perimeter of the lesion between the device halves; slicing the lesion from the skin with the blade above the device; and holding the excision site closed with the device.

The present invention also provides a skin-closure device including a pair of elongate legs, the device having an open condition in which the legs are distant and a closed condition in which the legs are proximate. Each of the legs is provided with at least one skin-piercing pin which extends toward the other leg. The device, in its closed condition, is retained to the skin by the pins.

The present invention also provides a skin-closure device including first and second separate halves, these halves having means for interfitting with each other without the interfitting means piercing the skin. The device has a first, open condition in which the halves are less than fully engaged with each other, a second, closed condition in which the halves are fully engaged with each other and retained together. At least one of the halves includes means for retaining the device to the skin without interconnecting the first and second halves.

The present invention also provides a skin lesion exciser including a blade, wherein excision of a skin lesion placed in proximity to the blade is effected by movement of the blade against the skin, a skin-closure device which holds the skin closed at the site of the excision after excision of the skin lesion from the skin, and means for excising the skin lesion from the skin with the blade and closing the skin with the device during movement of the blade.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is an oblique view of a first embodiment of the inventive device positioned against the skin of the patient and in a first state, prior to lesion excision, with the forceps retracted;

FIG. 2 shows the device of FIG. 1 in a second, sequential state, prior to lesion excision, with the forceps extended and capturing the lesion to be excised;

FIG. 3 shows the device of FIG. 1 in a third, sequential state, prior to lesion excision, with the forceps shown in a lesion-pulling position and the safety pin removed;

FIG. 4 shows the device of FIG. 1 in a fourth, sequential state, during lesion excision, with the staple partially closed through the skin surrounding the lesion;

FIG. 13 is an oblique view of the blade assembly of the device of FIG. 9;

FIG. 14 is an oblique view of the blade assembly of FIG. 13 fitted to the second applicator block of FIG. 12;

Corresponding reference characters indicate corresponding parts throughout the several views. The exemplifications set out herein illustrate various embodiments of the invention and such exemplifications are not to be construed as limiting the scope of the invention in any manner.

DETAILED DESCRIPTION OF THE INVENTION

Figure 5:
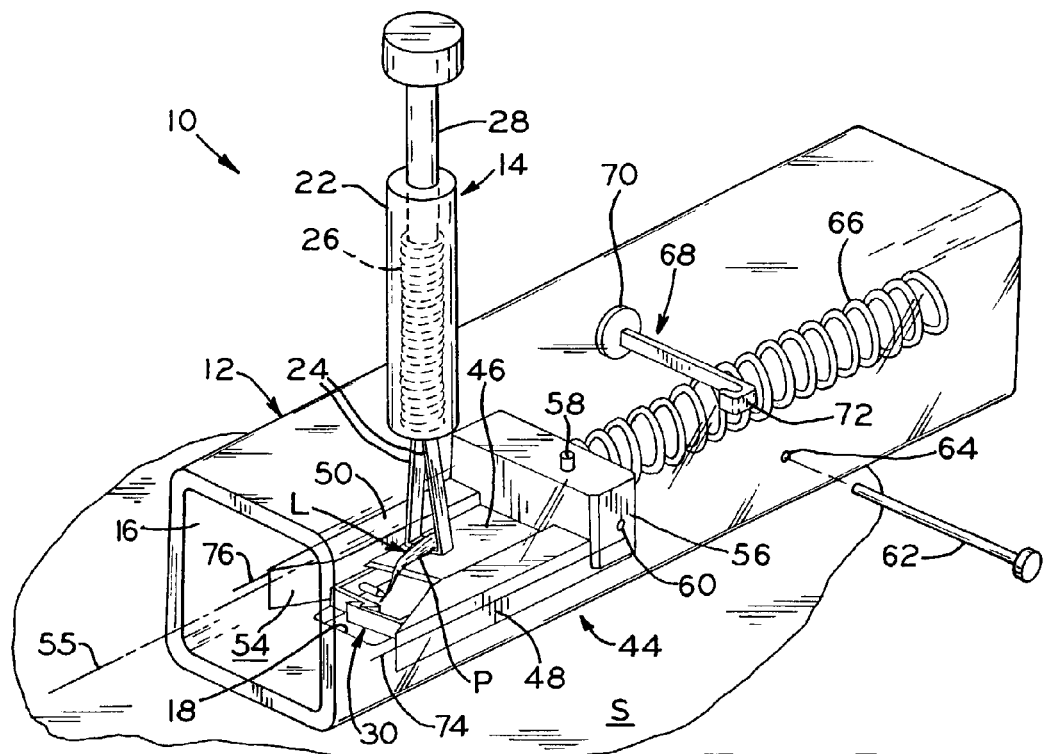
FIG. 5 shows the device of FIG. 1 in a fifth, sequential state, during lesion excision, with the staple more fully closed.

FIG. 1 shows exciser 10, a first embodiment of the present invention which includes base assembly 12 and separable forceps assembly 14. It is envisioned that exciser 10 may be a single use device, all or part of which may be discarded after a lesion has been excised therewith.

Base assembly 12 includes transparent, elongate plastic housing or frame 16 which, as shown, has the shape of a parallelepiped. It is envisioned, however, that housing 16 may be of any suitable shape. The lower side of housing 16, that side which, in use, lies against skin S of the patient, is provided with rectangular first aperture 18 which frames lesion L to be excised. At a location directly opposite first aperture 18, the upper side of housing 16 is provided with circular second aperture 20 into which the end of cylindrical body 22 of forceps assembly 14 is inserted.

Forceps assembly 14 further includes forceps or tweezers 24 having a pair of elongate, separable, somewhat flexible arms which are retractable into and extendable from the interior of cylindrical forceps body 22, and spring 26 which acts to urge tweezers 24 into the interior body 22. Forceps assembly 14 is also provided with plunger 28 which, when depressed with the thumb, urges tweezers 24 out of body 22 against the action of spring 26, the extended tweezers urged into an open position in which its arms are spread. Release of plunger 28 allows spring 26 to force tweezers 24 upwardly and into body 22, closing the tweezers. Those of ordinary skill in the art will recognize that forceps assembly 14 may include a mechanism similar to slender, elongate tools commonly used by mechanics for grasping small parts such as screws and nuts, for example, which have been dropped into hard to reach places. Such grasping tools typically employ spring-biased tweezers which are opened by depression of a plunger, as described above. Alternatively, forceps assembly 14 may include a mechanism (not shown) by which tweezers 24 are similarly extended from a body and opened, or retracted into the body and closed, by turning a screw threaded into the body, the tip of the screw attached to the tweezers inside the body. As a further, unshown alternative, second aperture 20 may be enlarged, or housing 16 otherwise adequately fashioned to allow the lesion to be manually captured with an ordinary pair of tweezers or forceps.

Disposed inside housing 16, adjacent to first aperture 18, is a skin-closure device which may be made of a surgical stainless steel or a suitable plastic material: Unitary staple 30, in its opened condition, is somewhat V-shaped, having a pair of distant, splayed straight legs, 32 and 34, each having an end integrally connected to central portion 36 which extends between one end of the legs. The free end of legs 32 and 34 are respectively provided with barbs 38 and 40 which, when the legs are proximate and the staple is closed, interlock and hold the staple in its closed condition. Staple 30 may be lightly adhered to the inside surface of housing 16 to help maintain its position prior to being closed.

The interfacing, or inward sides of legs 32 and 34 are provided with a plurality of pointed pins 42 which extend therefrom and which, when the staple is closed, are alternating relative to the legs from which they extend. When the staple is closed, and pins 42 extend through the skin below the excision site, the pointed free end of each pin 42 abuts or is at least proximal the inward side of the opposite leg. It is to be understood that staple 30, and/or any of the other skin-closure devices or staples described further herein below, are exemplary embodiments which may be adapted for use with the inventive excisers. It is envisioned that other types of skin-closure devices which serve to close or maintain closed the skin at the lesion excision site may also be in accordance with the present invention, and such devices or the use thereof fall within the scope of the present invention.

Housing 16 is provided with inverted U-shaped clip 43 (FIG. 8) which is integrally molded or otherwise attached thereto at the edge of rectangular first aperture 18 nearest blade assembly 44. Clip 43 surrounds three sides of staple central portion 36 to prevent its movement longitudinally of housing 16 when engaged by the blade assembly, as disclosed further below. Notably, the opening of clip 43 is located over first aperture 18 such that, upon removal of base assembly 12 from the skin of the patient after excision of the lesion, closed staple 30 may exit the housing with clearance between its central portion 36 and the adjacent edge of first aperture 18. Note that excisers and skin-closure devices of different sizes may be provided to accommodate the excision various sized lesions and closure of skin at the excision site.

Also disposed within housing 16 is blade assembly 44 which includes surgical steel blade 46 fixed between wedges or hammers 48 and 50. Hammers 48 and 50 are staple-engaging portions of blade assembly 44 and are provided with surfaces 52 and 54 which are curved or flat and are oblique to the longitudinal axis 55 of housing 16. As will be described further hereinbelow, during actuation of exciser 10, hammers 48 and 50 and blade 46 move coincidentally such that surfaces 52 and 54 slidably engage legs 32 and 34 of staple and move legs 32 and 34 together, thereby closing the staple and the skin simultaneously with the excision of the lesion from the skin by blade 46. Notably, the sharp edge of blade 46 is located adjacent to surfaces 52 and 54, and slicing of the lesion from the skin occurs as opposite portions of legs 32 and 34 along axis 55 are squeezed together by surfaces 52 and 54 to their closed distance from each other. Notably, too, above-described clip 43 is located well beneath blade 46 so that the clip will not interfere with the blade's movement.

Blade assembly 44 further includes block 56 to which hammers 48 and 50 and blade 46 are attached. Block 56 is provided with post 58 which extends vertically and hole 60 (FIGS. 3-7) which extends laterally. Base assembly 12 is also provided with removable elongate safety pin 62 which, prior to actuation of exciser 10, extends into hole 60 and through hole 64 in housing 16.

Compression spring 66 is provided inside housing 16, and has one end fixed relative to the housing; the other end abuts block 56. Spring 66 thus urges blade assembly 44 from its cocked position along axis 55 toward staple 30. With safety pin 62 installed, blade assembly 44 is retained in its cocked position against the force of compression spring 66 and may not be inadvertently actuated or triggered. With safety pin 62 installed, blade assembly 44 thus may not be slidably moved within housing 16 along axis 55. Base assembly 12 also provided with plunger 68 which extends through the lateral wall of housing 16 and has head 70, the depression of which triggers blade assembly 44 once safety pin 62 has been removed.

Plunger 68 is provided with J-shaped latching end or hook 72 which, in the blade assembly cocked position, partially surrounds post 58, the free end of hook 72 extending laterally in a direction perpendicular to axis 55 and abutting the post. Depression of plunger head 70 moves plunger 68 laterally such that post 58 is no longer captured within hook 72 and, with safety pin 62 removed, spring 66 will then immediately force blade assembly 44 to move along axis 55 toward the lesion and staple 30.

The operation of exciser 10 will now be described with sequential reference to FIGS. 1-7. The body 16 of base assembly 12 is placed against skin S of the patient such that lesion L to be excised is framed by aperture 18, and safety pin 62 is removed. Referring to FIG. 2, plunger 28 of forceps assembly 14 is depressed against spring 26 and tweezers 24 are extended into the interior of housing 16 and expand. The free ends of tweezers 24, which may be serrated for enhanced gripping ability, acquire or grab the lesion and, with reference to FIG. 3, plunger 28 is released. Under the influence of spring 26, tweezers 24 are at least partially retracted into cylindrical body 22 and pull the lesion upwardly through aperture 18. Parallel lines 74 and 76 are etched or printed onto the transparent lateral sides of body 16, and blade 46 lies and moves in a plane containing lines 74 and 76; these lines thus establish the location on the skin at which the lesion will be excised by the blade.

Figure 8:
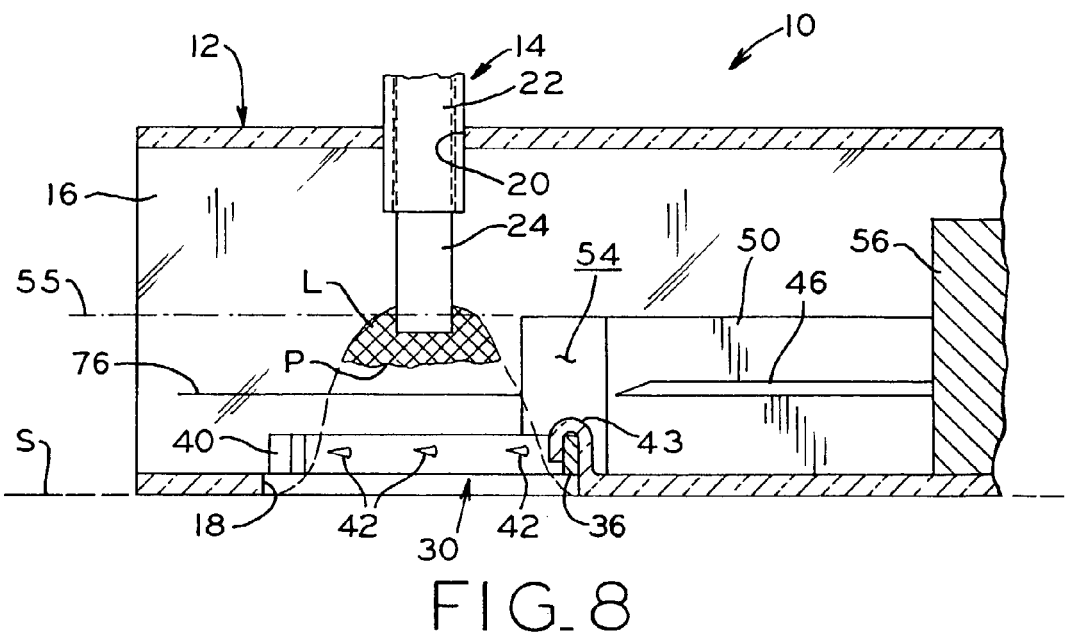
FIG. 8 is an enlarged fragmentary sectional view of the exciser of FIG. 1 along line 8-8, showing the staple retention feature of the housing and the position of a lesion to be excised from the skin.

Because body 16 is transparent, the doctor or nurse practitioner can establish the desired elevated position of the lesion by first sighting lines 74 and 76 laterally through the body such that they are viewed as being superposed, and adjusting the lesion with forceps assembly 14, if and as necessary, such that perimeter P of lesion L, which may be irregularly shaped, is pulled to a position above the superposed lines, as best shown in FIG. 8. So positioned, the lesion will, after actuation of the blade assembly, be placed in proximity to blade 46 which cuts the skin located outside lesion perimeter P. In adjusting forceps assembly 14, its body 22 may be moved relative to base assembly housing 16, or its plunger 28 may be pulled further upward, drawing tweezers 24 further into body 22. Alternatively, as mentioned above, the lesion may be captured manually using an ordinary pair of tweezers or forceps and appropriately positioned prior to triggering blade assembly 44. As a further alternative, the lesion may be captured with a skin hook (not shown) and appropriately positioned prior to triggering the blade.

Once the lesion is in its desired position within housing 16, blade assembly 44 is triggered by depression of plunger head 70. In immediate response to the free end of plunger hook 72 sliding clear of block post 58, blade assembly 44 quickly moves along axis 55. Blade 46 passes below the free ends of tweezers 24 and through the skin outside of lesion perimeter P, slicing the lesion from the skin while staple 30 simultaneously closes the skin at a location below the excision site. During closure of staple 30, as surfaces 52 and 54 of hammers 48 and 50 slidably engage and close legs 32 and 34, pins 42 pierce and protrude through the skin of the patent, and hold the staple in place and prevent it from being pulled from the re-approximated skin after closure. During the simultaneous excision and closure, the shorn edges of the skin on opposite sides of the excision are captured between staple legs 32, 34, and are upwardly diverted, resulting in a desirable, elliptically-shaped closure. Further, the dermis of these shorn skin edges, rather than merely the epidermis, is brought into abutting contact, thereby allowing the stronger parts of the skin to mend together and speeding the excision site healing time.

Figure 6:
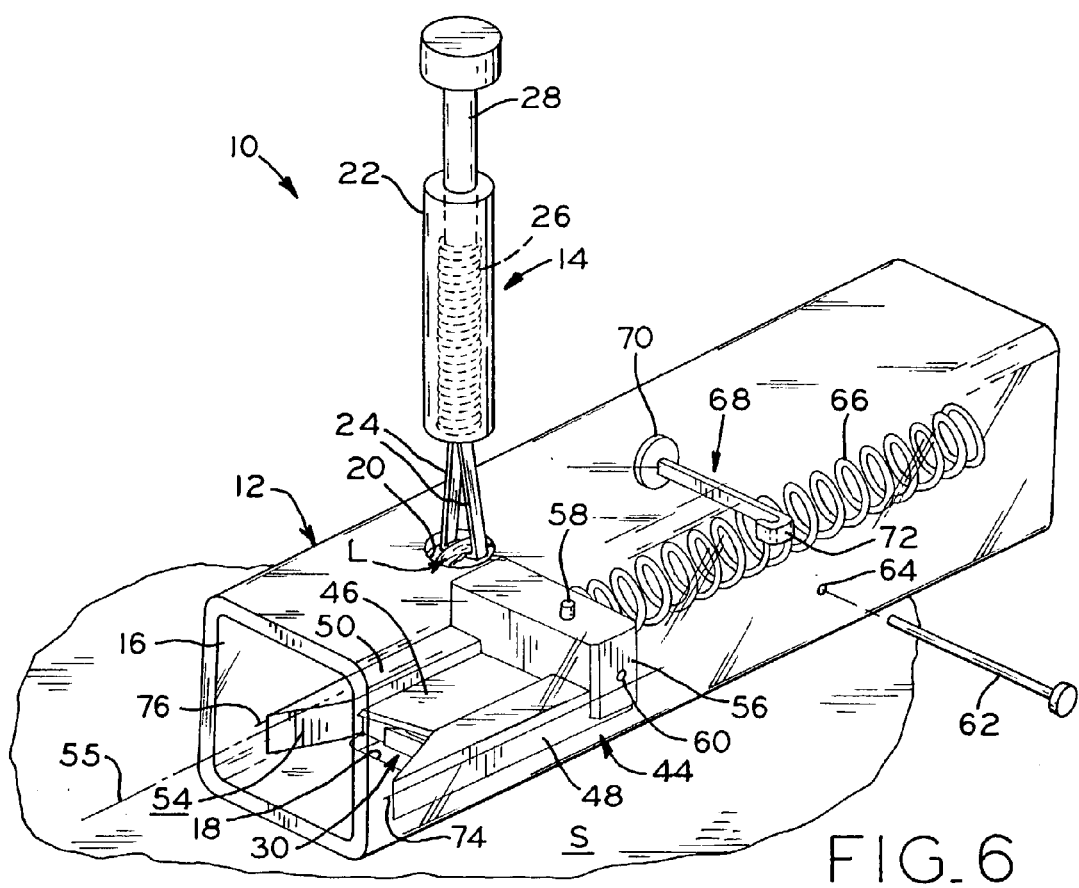
FIG. 6 shows the device of FIG. 1 in a sixth, sequential state, after lesion excision, with the staple fully closed, the forceps being withdrawn from the device and removing the lesion from the skin.
Figure 7:
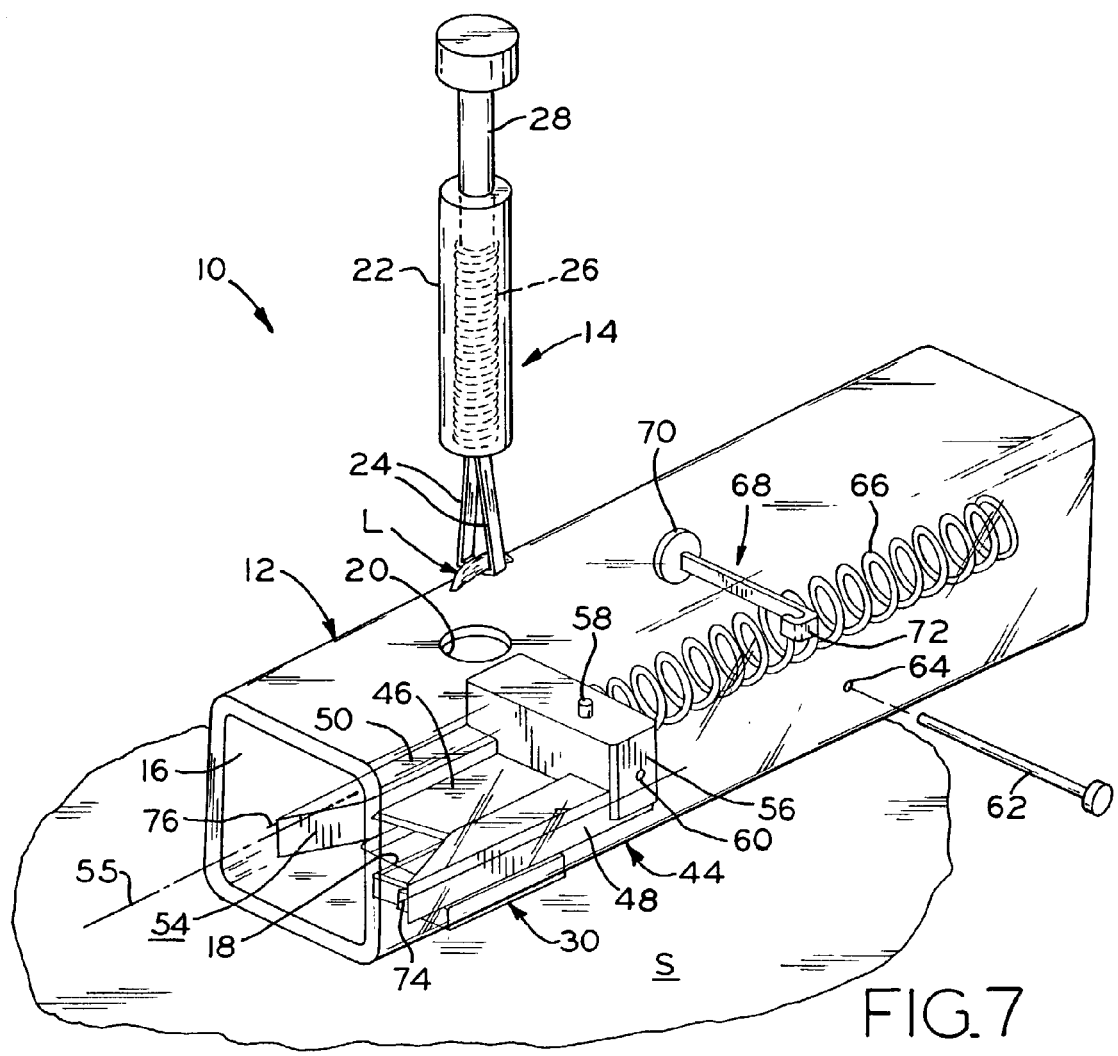
FIG. 7 shows the device of FIG. 1 in a seventh, sequential state, after lesion excision, the device housing being removed from the skin, the forceps holding the excised lesion fully removed from the device housing.

Referring to FIGS. 5 and 6, the flat interfacing and parallel surfaces of hammers 48 and 50 are spaced such that central portion 36 of staple 30 fits closely therebetween and when barbed ends 38 and 40 of the staple become interlocked, the staple will assume a rectangular shape which is smaller than the periphery of rectangular first aperture 18. After blade assembly 44 has traveled its entire distance along axis 55, the lesion will be fully excised from the skin and staple 30 is completely closed. Base assembly 12 may then be removed from the patient's skin, closed staple 30 passing through first aperture 18. Forceps assembly 14, still gripping the excised lesion, may then be withdrawn from hole 20 of housing 16. In FIG. 7, forceps assembly 14 is shown having been completely and separably withdrawn from base assembly 12 with the excised lesion captured between the ends of tweezers 24. The excised lesion may then be discarded or sent to a laboratory for biopsy or other analysis as appropriate.

It is envisioned that after approximately four days the excision wound will have sufficiently healed that staple 30 may be removed. Staple 30 may be removed by cutting it, perhaps at its central portion 36, and peeling its legs 32, 34 away from the skin and withdrawing pins 42 therefrom.

Referring now to FIGS. 9-21, there is shown exciser 100, a second embodiment of the present invention which was prototyped and successfully used in animal experiments.

Exciser 100 comprises first applicator block 102 and second applicator block 104. Disposed between the applicator blocks is blade assembly 106. Guide rods 108 are fixed within bores 110 provided in first applicator block 102 and slidably extend through bores 112 in second applicator block 104. First and second applicator blocks 102 and 104 may be made of a polymeric material such as nylon, for example.

Blade assembly 106 comprises block portion 114 and blade 116. Block portion 114 is made of a material similar to that of applicator blocks 102, 104, and blade 116 is surgical steel or suitable plastic material, like blade 46 of first embodiment exciser 10. Blade 116 is attached to block portion 114 through means of fastener 120 or by any other suitable means. Guide rods 108 slidably extend through bores 118 provided in blade assembly block portion 114.

Figure 10:
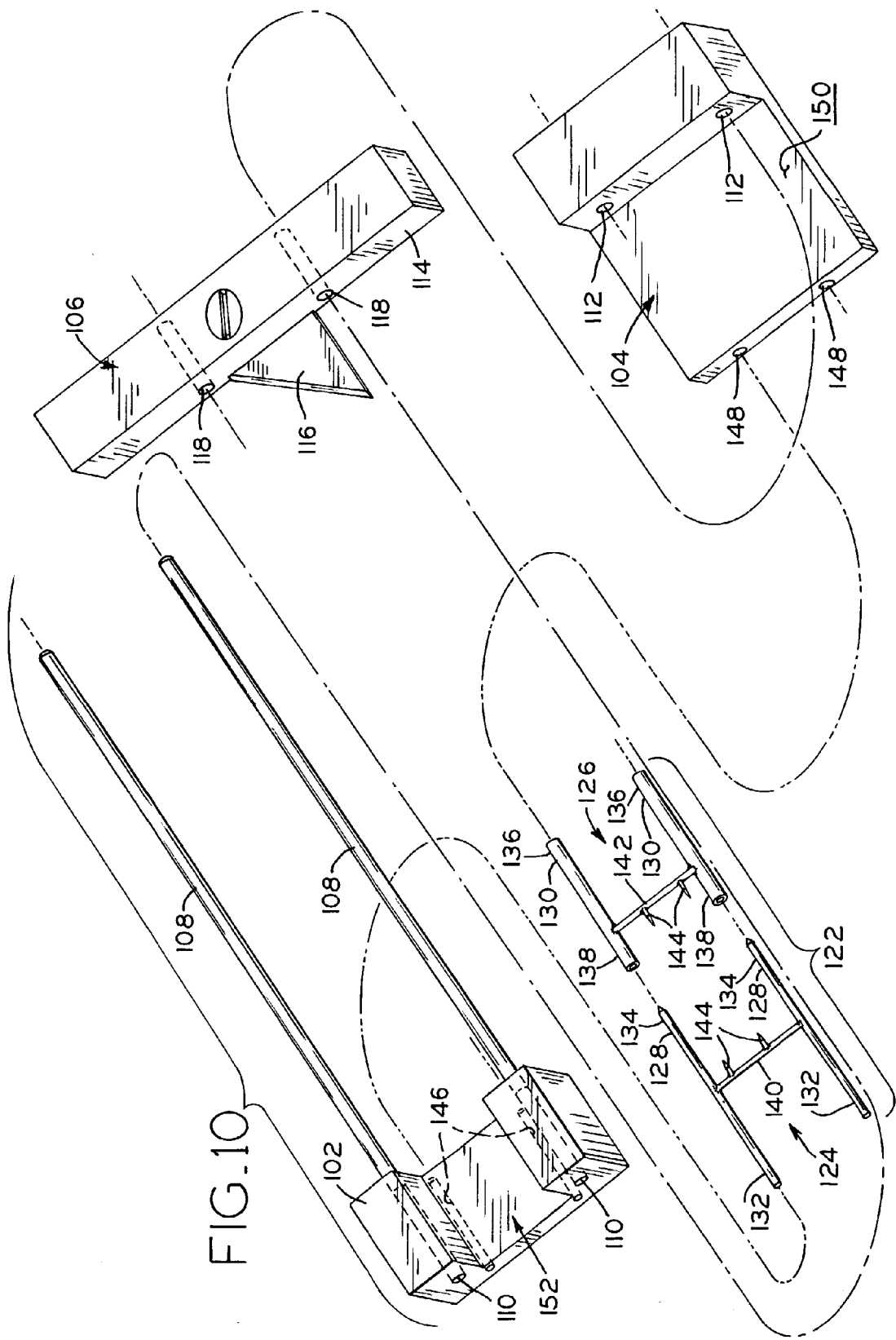
FIG. 10 is a view of the component parts of the device of FIG. 9 in a disassembled state.
Figure 11:
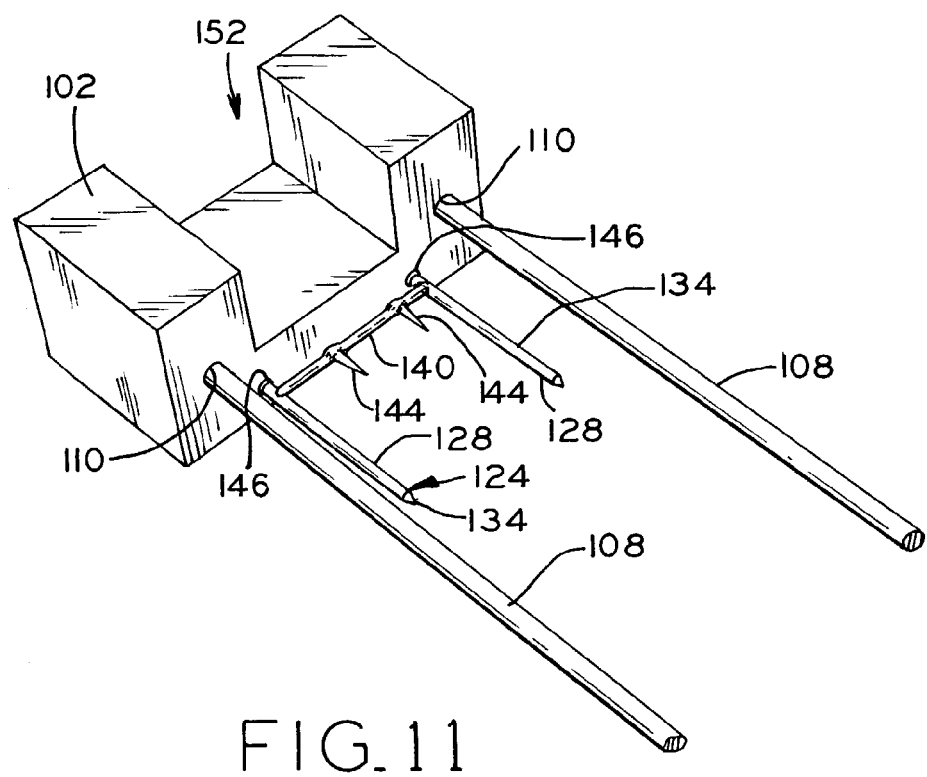
FIG. 11 is an oblique view of the first applicator block of the device of FIG. 9, with the male staple half inserted therein.
Figure 12:
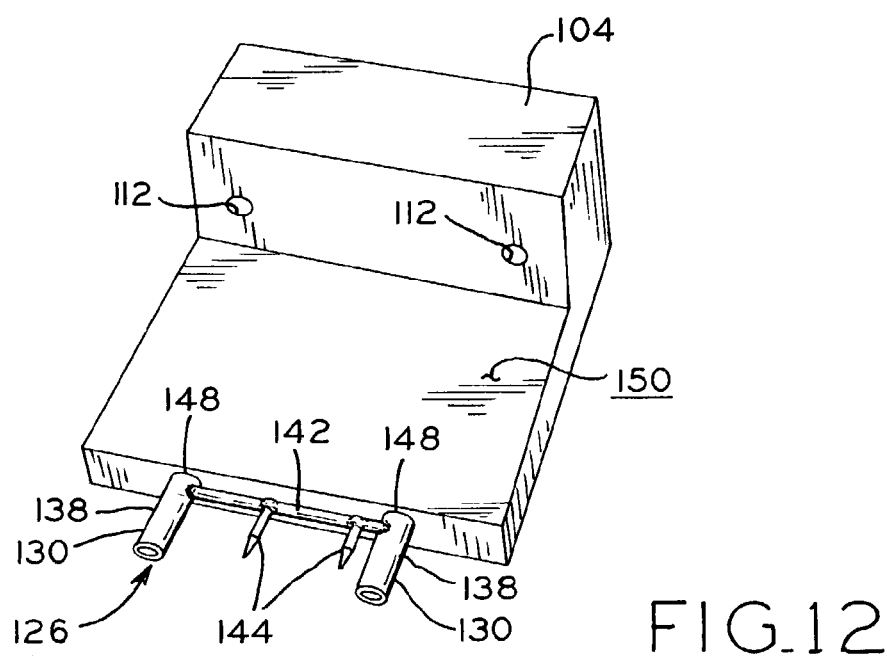
FIG. 12 is an oblique view of the second applicator block of the device of FIG. 9, with the female staple half inserted therein.

The basic components of exciser 100 and its associated skin-closure device are shown in FIG. 10. Two-part staple 122 comprises interfitting male half 124 and female half 126. Male staple half 124 comprises a pair of parallel rod portions 128, and female staple half 126 comprises a pair of similarly spaced parallel tube portions 130. Rod portions 128 each include extending portion 132 and pointed engaging portion 134. Tube portions 130 each include extending portion 136 and engaging portion 138. As further described hereinbelow, each solid engaging portion 134 of the male staple half slidably and interferingly engages its mating hollow engaging portion 138 of female staple half 124 during closure of the staple. When staple halves 124 and 126 are separated or less than fully seated, staple 122 is in its open condition, and when staple halves 124 and 126 are fully engaged, staple 122 is in its closed condition. The interference fit between engaging portions 134 and 138 ensure that staple 122 remains in its closed condition after excision of the lesion.

Figure 15:
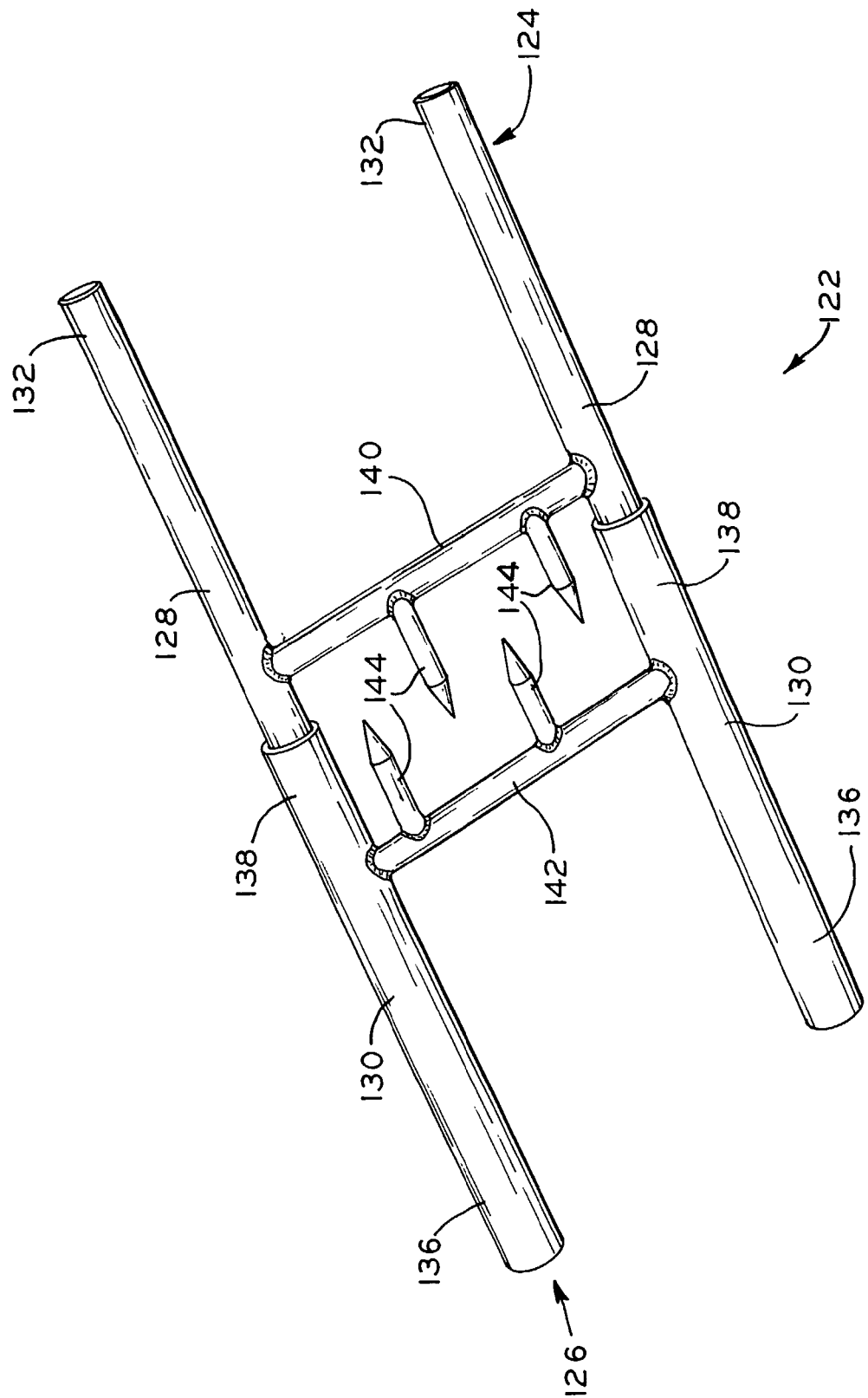
FIG. 15 is a view of the male and female staple halves of FIGS. 11 and 12, respectively, shown interfitted.

Extending between and fixed to rod portions 128 of male staple half 124 is elongate leg 140, and extending between and fixed to tube portions 130 of female staple half 126 is elongate leg 142. When fitted into exciser 100, or when staple 122 is closed, legs 140 and 142 are parallel and extend in directions perpendicular to the longitudinal directions of rod and tube portions 128, 130. Each of legs 140 and 142 is provided with a plurality of sharpened pins 144, which correspond to pins 42 of first embodiment exciser 10 shown in FIGS. 1 through 8. Pins 144 extend in the longitudinal directions of engaging portions 134 and 136 and, when the staple 122 is closed, the pins of the male and female staple halves are misaligned such that they alternate along the legs, and the pointed tips of the pins of one staple half are in close proximity to the leg of the opposite staple half. Notably, when staple 122 is closed as shown in FIG. 15, engaging portions 134 of male staple half 124 extend beyond the engaging portion 138 of female staple half 126 and into the female staple half's tubular extending portions 136. The distance between parallel legs 140 and 142 when staple 122 is closed may be limited by the length of female staple half engaging portion 138 relative to its leg 142, i.e., the ends of engaging portions 136 abut leg 140, thereby minimizing the distance between the staple legs.

Referring again to FIG. 9, it can be seen that prior to excision of lesion L from skin S, extending portions 132, 136 of respective male and female staple halves 124, 126 are received into holes 146, 148 in first and second applicator blocks 102, 104, respectively. That is, holes 146 receive extending portions 132 of male staple half 124, and the male staple half is slid into first applicator block 102 until the interfacing surfaces of the first applicator block and leg 140 abut. Similarly, extending portions 136 of female staple half 126 are slidably received in holes 148 provided in second applicator block 104, with the interfacing surfaces of the second applicator block and leg 142 abutting.

Figure 9:
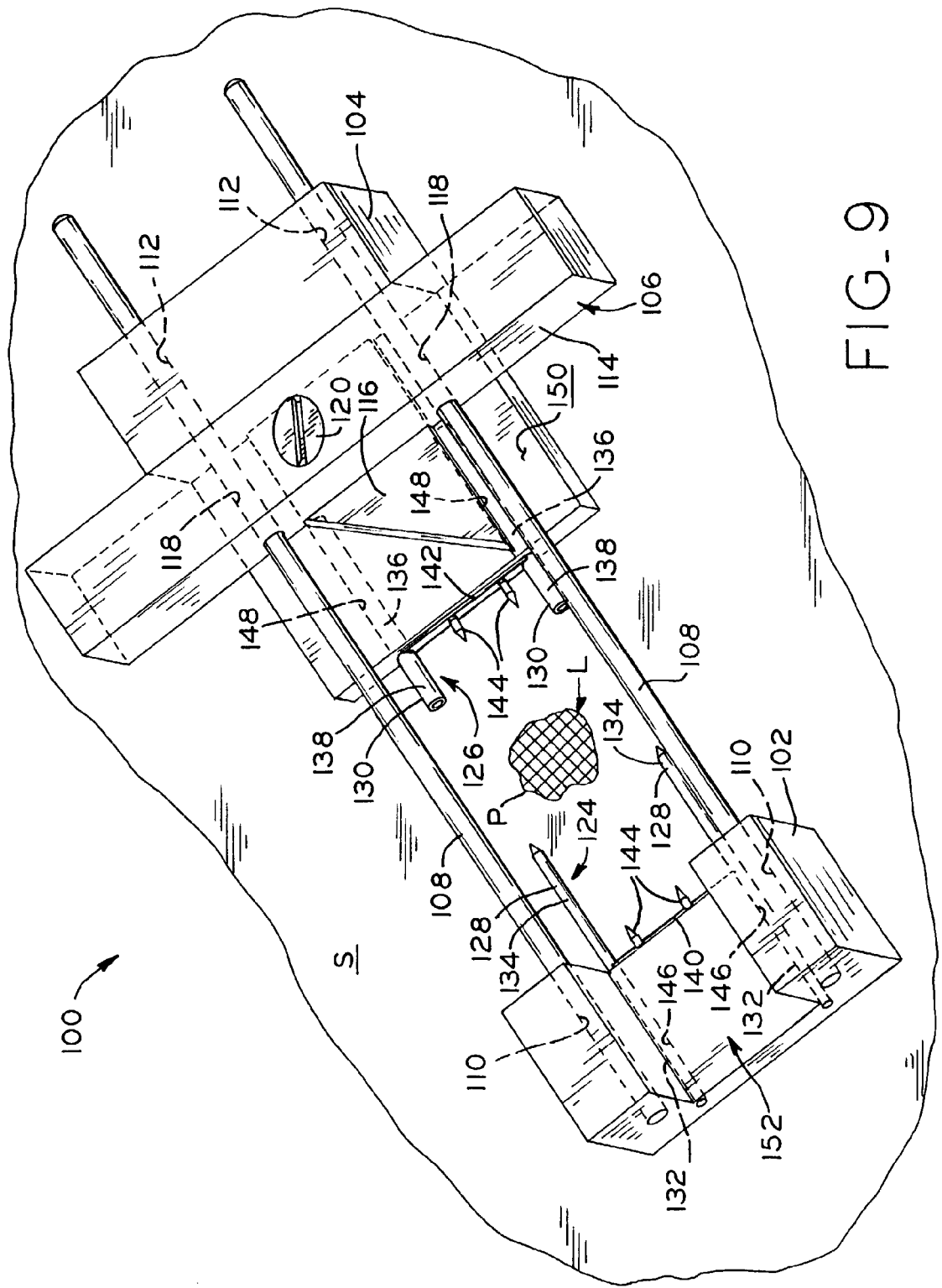
FIG. 9 is an oblique view of a second embodiment of the inventive device located on the skin of the patient, assembled and in a first, open position.
Figure 16:
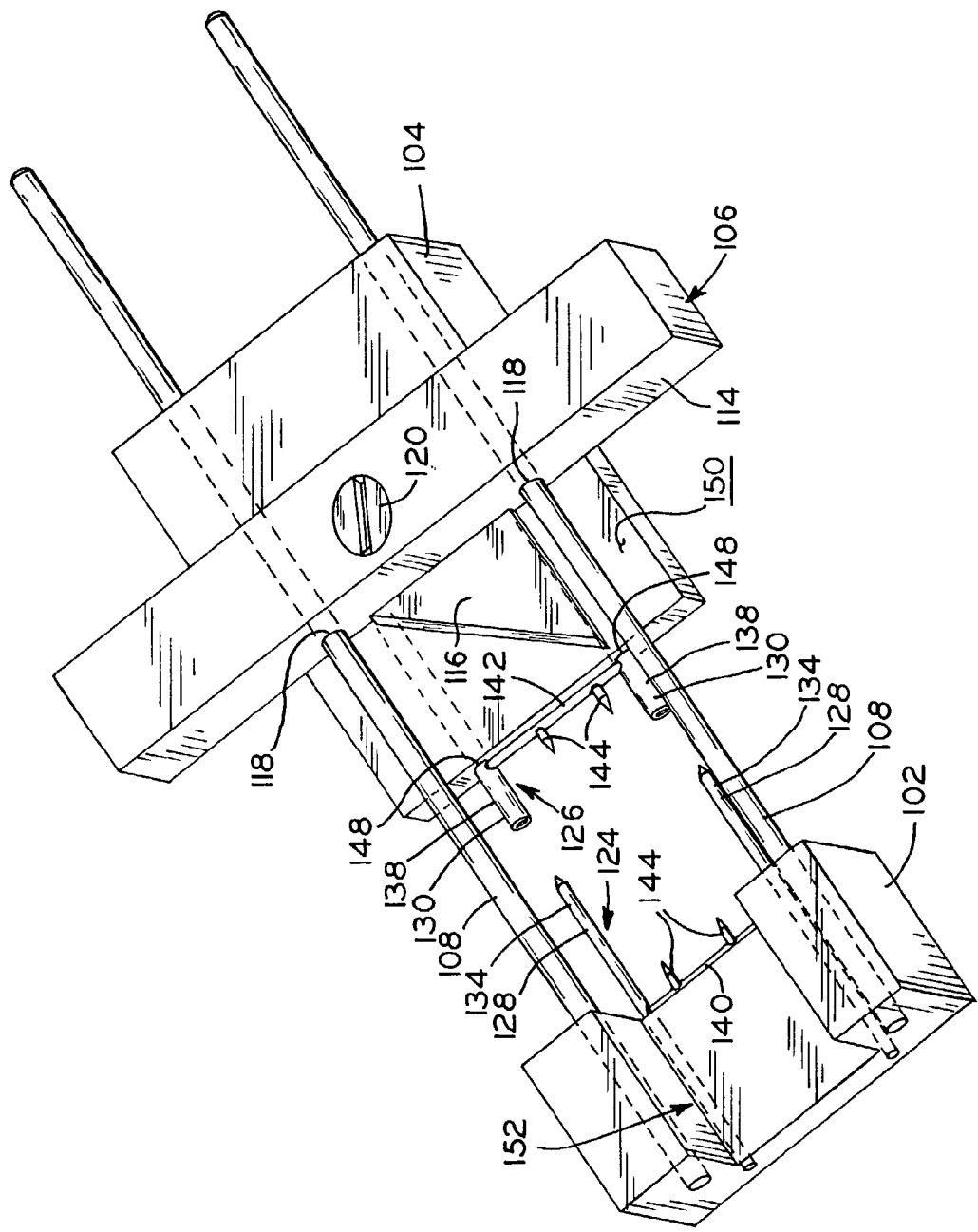
FIG. 16 shows the device of FIG. 9 in a first state, prior to lesion excision.

FIGS. 9 and 16 show exciser 100 loaded with a staple 122 and in its open condition, in which legs 140 and 142 are distant. So configured, exciser 100 is placed onto skin S of the patient. Perimeter P of lesion L to be excised is framed between legs 140 and 142 of the staple and also between the parallel engaging portions 134 of the male staple half 124. Is it again noted that excisers and staples of different sizes may be provided to accommodate the excision various sized lesions and closure of the excision site. During operation of exciser 100, first applicator block 102 is held stationary relative to the patient's skin and second applicator block 104 and blade assembly 106 are moved relative to first applicator block 102 along guide rods 108.

Lesion L to be excised with exciser 100 may be pulled away from skin S through a means of ordinary tweezers or forceps (not shown). Alternatively, the lesion may be captured and pulled away from the skin with a skin hook (not shown). Lesion L is pulled through exciser 100, between the staple legs and the engaging portions of the male staple half, to an extent which places its perimeter P on the side of the plane defined by blade 116 opposite that on which staple 122 is located. This ensures that the entire lesion, and not just a portion thereof, will be excised by blade 116 and the staple will close the skin beneath the excision site by pinching together, between proximate legs 140, 142, only skin located outside of perimeter P. As described above, the sharpened pins of the staple pierce the skin and hold the staple in place on the patient during healing. The excision site is closed by staple 122 into an elliptical shape, and the dermis of the skin, rather than merely the epidermis is brought into and held in abutting contact by the closed staple to promote faster healing.

Referring to FIGS. 16-20, the sequence of movements of exciser 100 and its staple halves are shown sequentially. Prior to the cutting of the skin by blade 116, it can be seen (FIGS. 16-18), that planar blade 116 overlies flat surface 150 of second applicator block 104 and thus cannot begin cutting engagement with the patient's skin until blade assembly 106 is moved relative to second applicator block 104 along guide rods 108.

Figure 17:
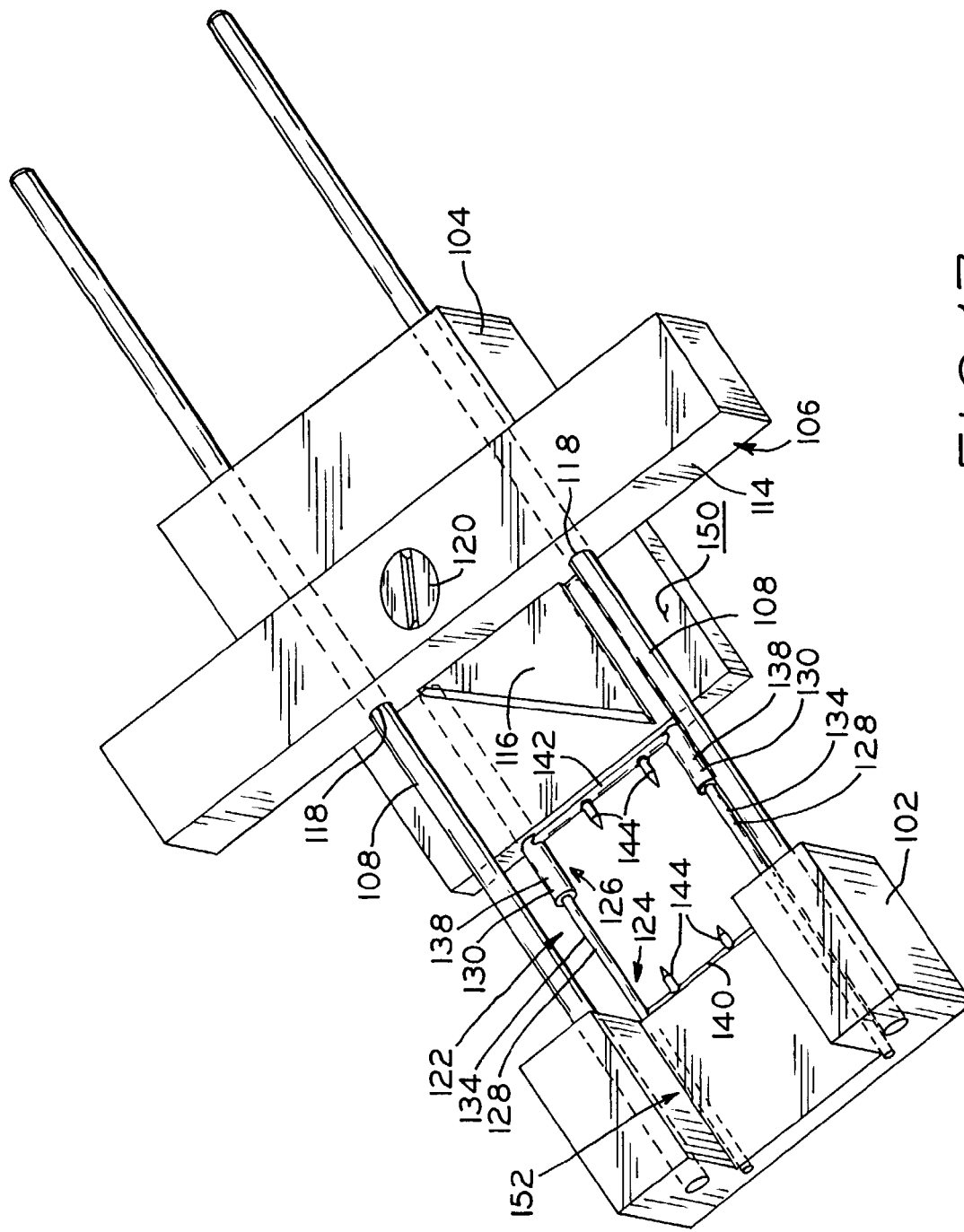
FIG. 17 shows the device of FIG. 9 in a second, sequential state, prior to lesion excision and during interfitting of the staple halves.

FIG. 17 shows the second applicator block 104 and blade assembly 106 having been moved together along guide rods 108 toward first applicator block 102 such that engaging portions 134 and 138 of male and female staple halves 124 and 126 have entered into partial engagement. Thus, it can be seen that closure of staple 122 has begun prior to any cutting by blade 116.

Figure 18:
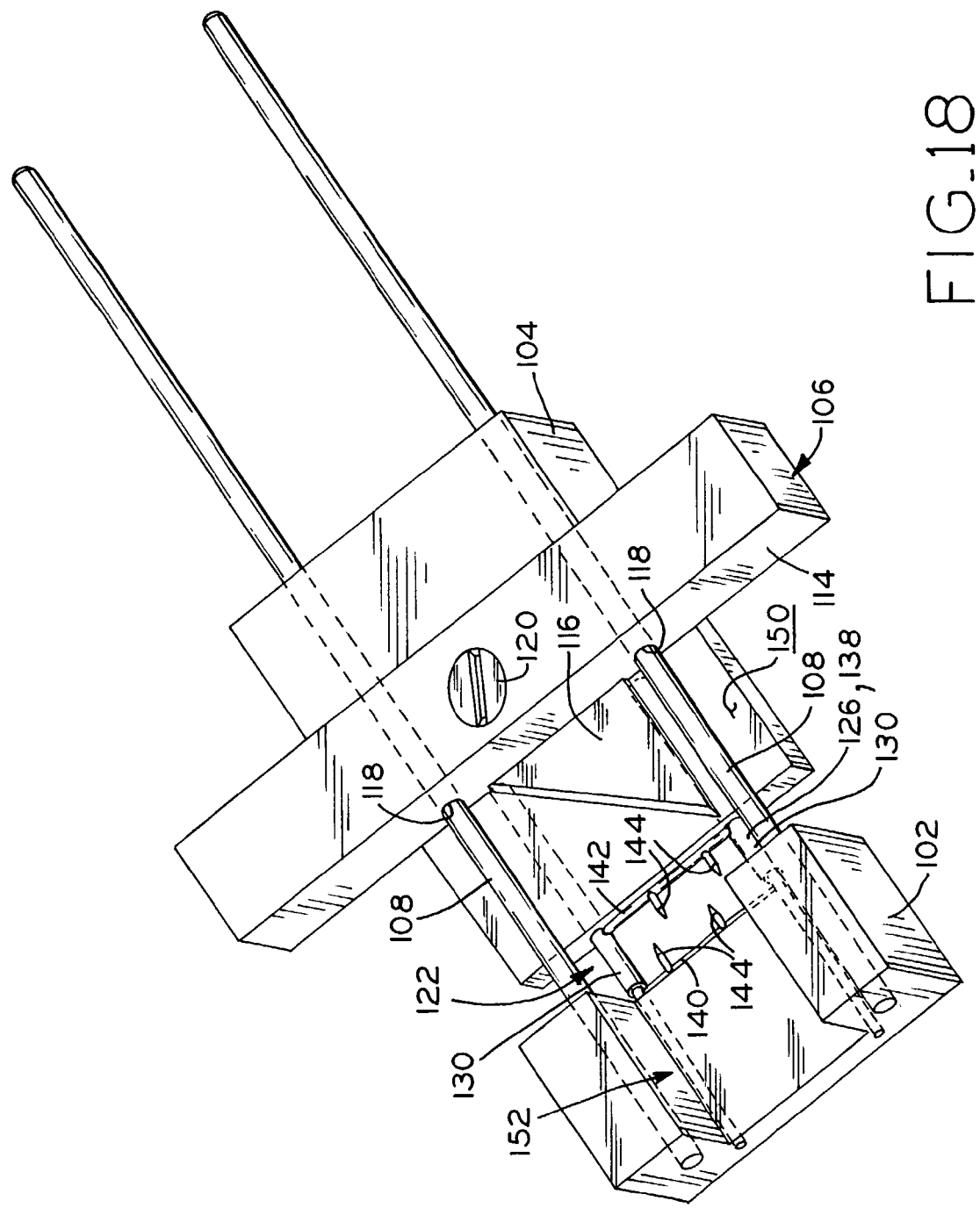
FIG. 18 shows the device of FIG. 9 in a third, sequential state, prior to lesion excision but after closure of the staple.

FIG. 18 shows that further movement of second applicator block 104 and blade assembly 106 together along guide rods 108 toward first applicator block 102 has completely closed staple 122, applicator blocks 102 and 104 being in their closest proximity to each other. Notably, unlike first embodiment exciser 10, in which excision of the lesion and closure of the excision site are done substantially simultaneously, exciser 100 completely closes staple 122 prior to any cutting by blade 116. Lesion L, which had previously been pulled outwardly away from the rest of the patient's skin by ordinary tweezers or forceps, is held in place such that its perimeter P is above the plane defined by flat blade 116 by the staple. Pins 144, which pierce the skin, support the lesion above the plane defined by flat blade 116; but the lesion may still be grasped by the tweezers or forceps for easy handling after excision.

Figure 19:
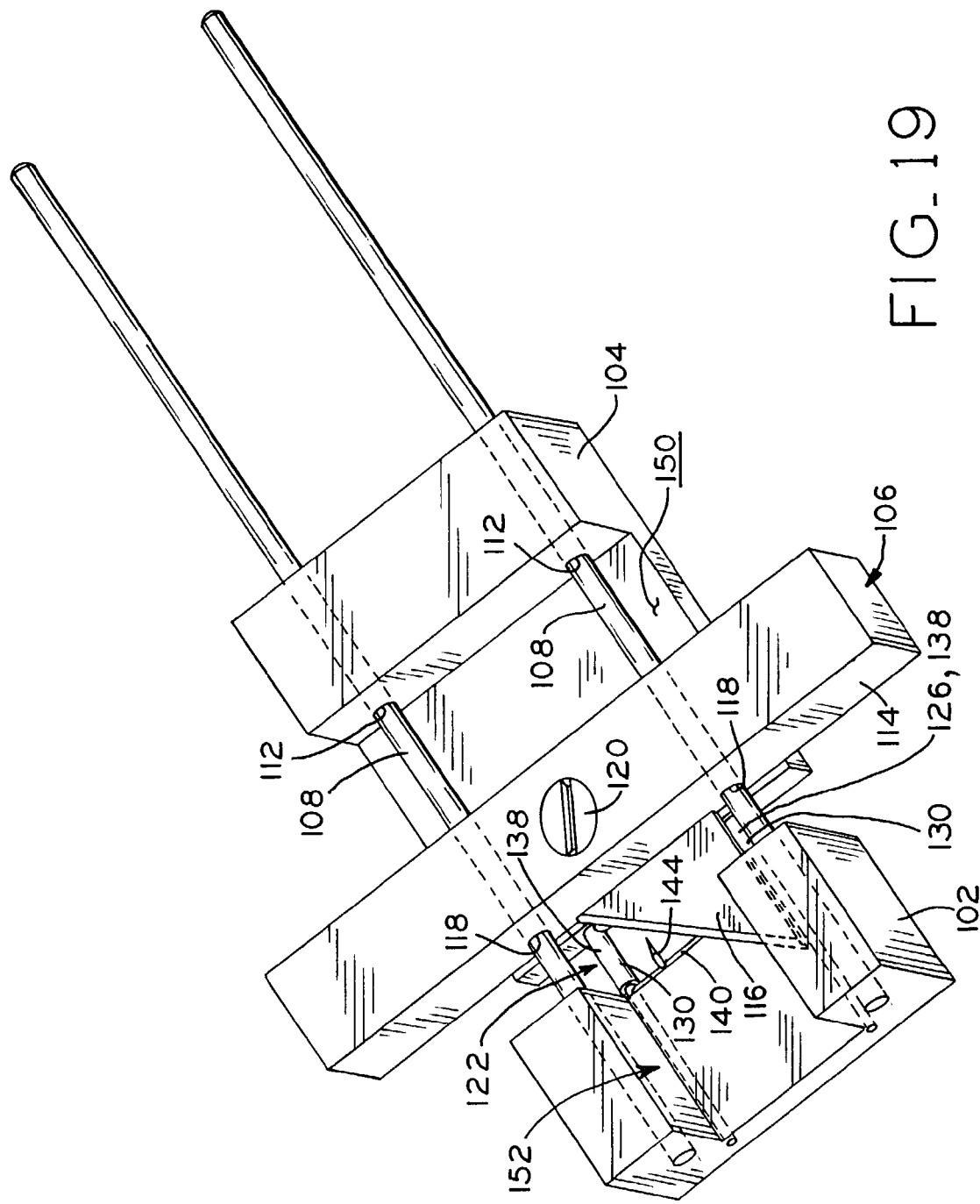
FIG. 19 shows the device of FIG. 9 in a forth, sequential state, during lesion excision.

Referring to FIG. 19, it can be seen that movement of blade assembly 106 relative to second applicator block 104 along guide rods 108 and toward first applicator block 102 forces blade 116 over the closed staple and through the patient's skin, preferably outside of the perimeter of the lesion. Here it can be seen that as blade 116 is moved, it is received in recess 152 formed in first applicator block 102.

Figure 20:
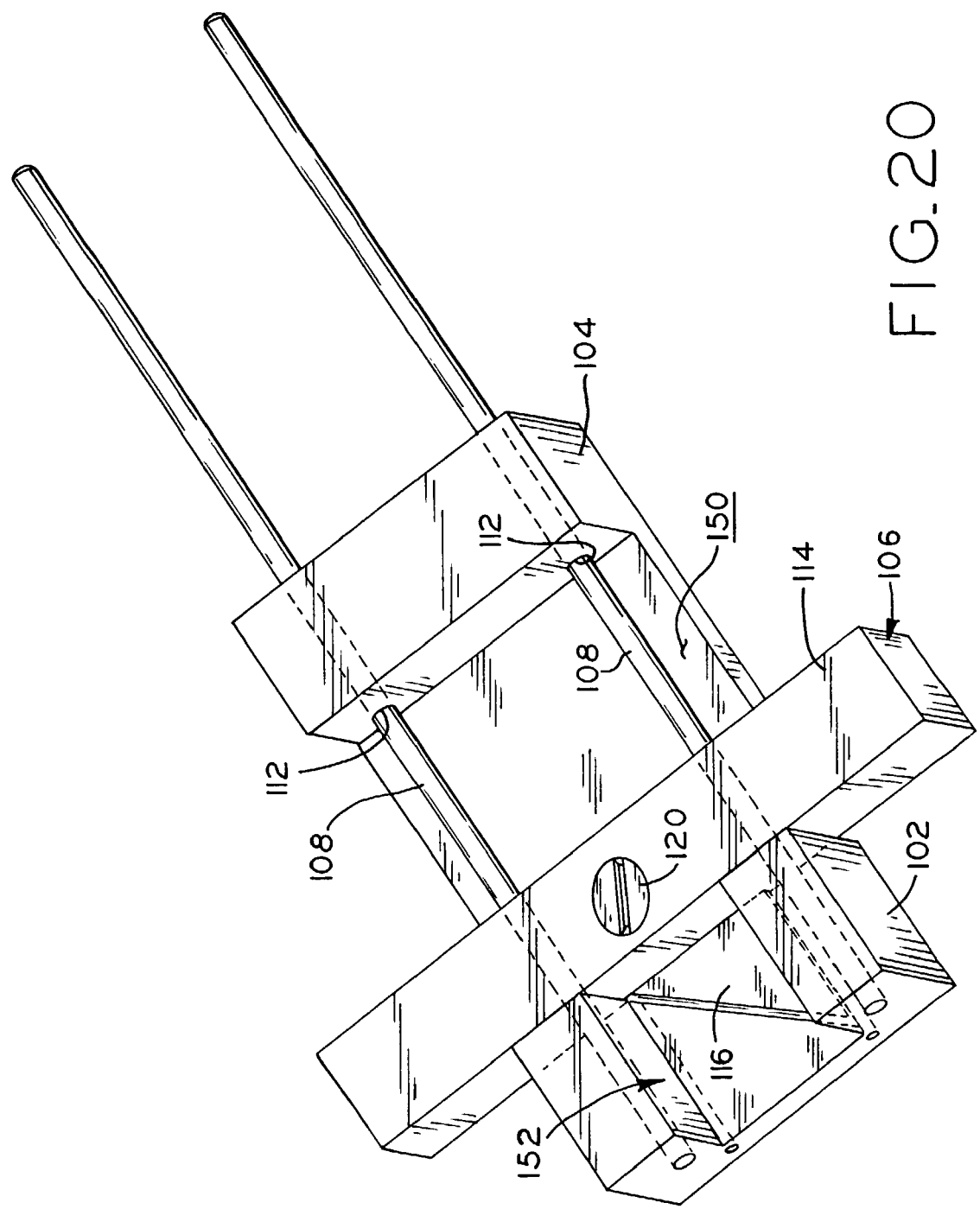
FIG. 20 shows the device of FIG. 9 in a fifth, sequential state, upon lesion excision.

Referring to FIG. 20, exciser 100 is shown in a position in which the lesion has been completely severed and perhaps removed from the excision site by the tweezers or forceps. In this position, the interfacing surfaces of first applicator block 102 and blade assembly block portion 114 abut, and further movement of blade assembly 106 along guide rods 108 away from second applicator block 104 is prevented.

Figure 21:
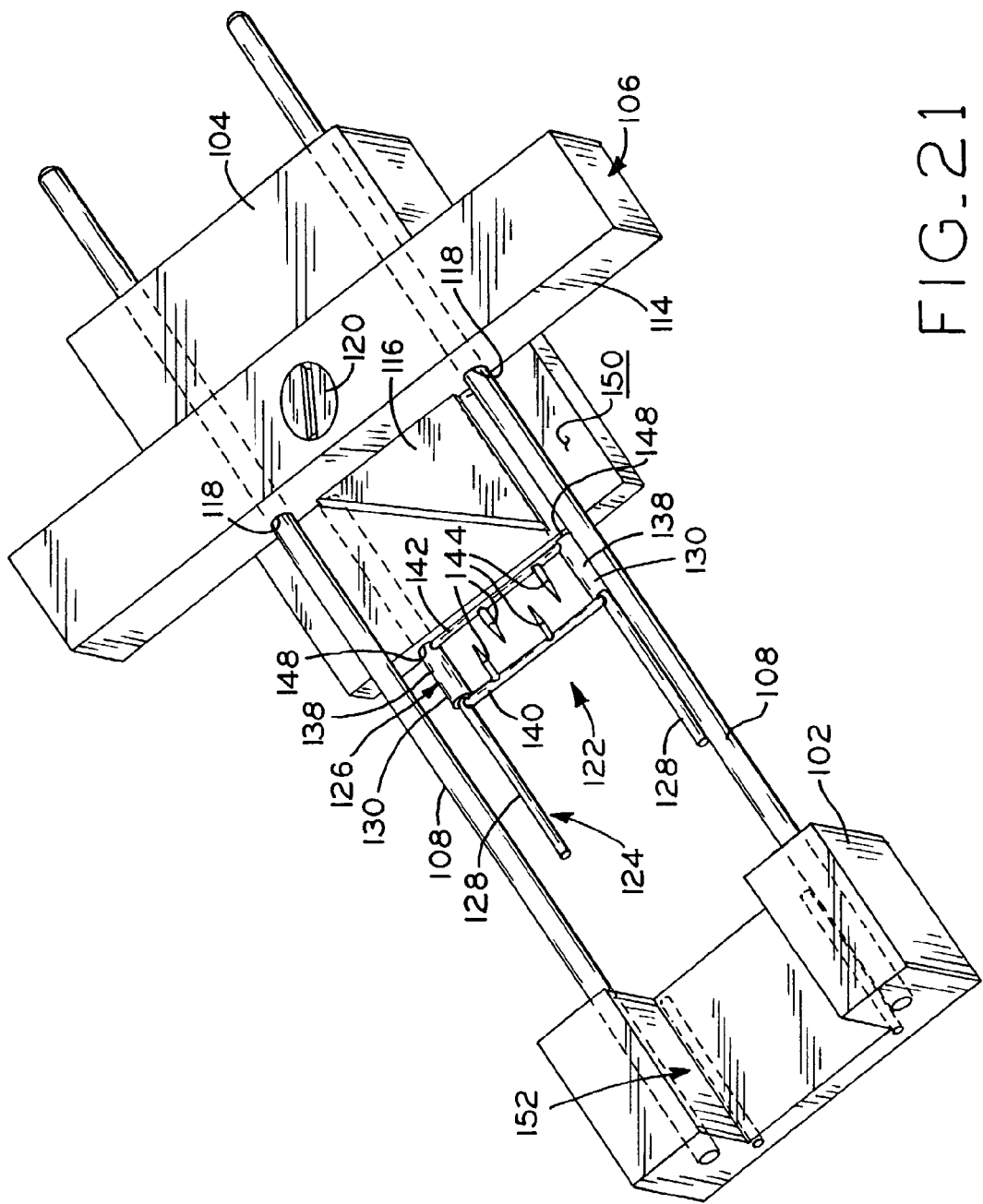
FIG. 21 shows the device of FIG. 9 in a sixth, sequential state, after upon completion of the excision and during partial release of the closed staple from the device.
Figures 22, 23:
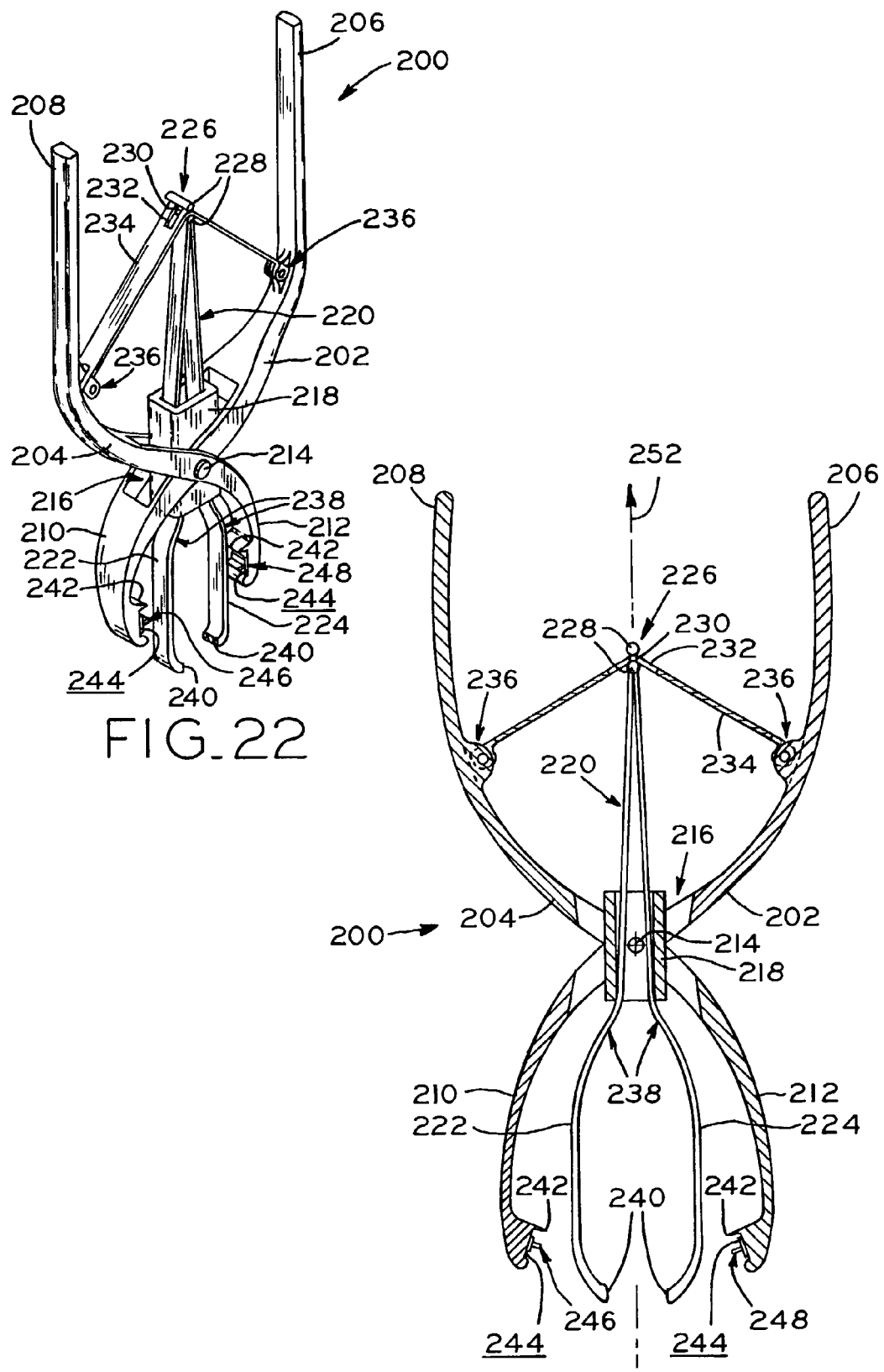
FIG. 22 is an oblique view of a third embodiment of the inventive device.
FIG. 23 is a sectional view of the device of FIG. 22 in a fully opened state.
Figure 24:
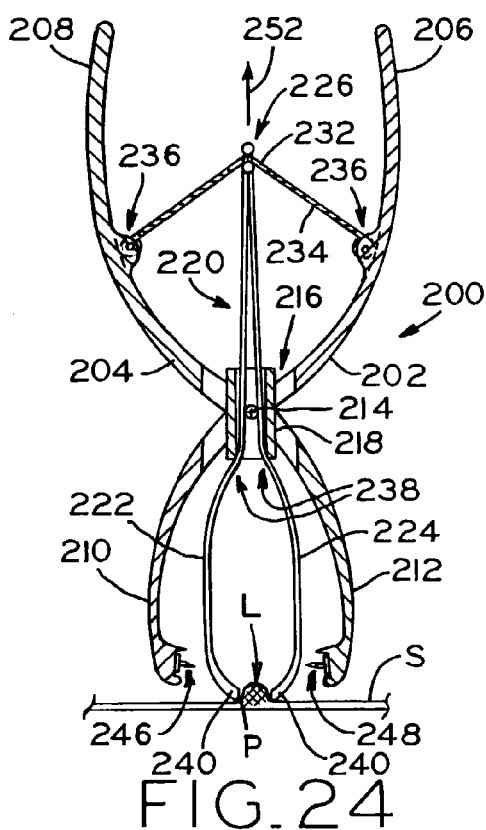
FIG. 24 is a sectional view of the device of FIG. 22 in a first state, prior to lesion excision, the integral tweezers or forceps of the device closed on the lesion to be excised.

Finally, with reference to FIG. 21, blade assembly 106 is reversely slid along guide rods 108 back to its initial position relative to second applicator block 104, and second applicator block 104 and blade assembly 106 are held together. First applicator block 102 is moved away from second applicator block 104 and blade assembly 106, withdrawing guide rods 108 therefrom. Extending portions 132 of staple 122 are withdrawn from holes 146 in first applicator block 102. The position of staple 122 of course remains stationary relative to skin S. Extending portions 136 of staple 122 are then withdrawn from holes 148 in second applicator block 104 and the exciser completely removed from the patient. The extending portions of staple 122 may then be trimmed to reduce the size of the staple. As noted above, it is anticipated that staple 122 would remain in place for approximately four days while the excision site heals, after which the staple halves may be separated by pulling them apart, overcoming the interference fit between the engaging portions 134 and 136. Alternatively, the staple may be cut in any convenient manner such that it may be removed in pieces from the patient.

Referring now to FIGS. 22-27 there is shown exciser 200, a third embodiment of the present invention which is formed of elongate first and second halves 202 and 204, each respectively having a handle portion 206, 208 and a jaw portion 210, 212. First and second halves 202 and 204 are pivotally joined together through rivets 214 to form a basic structure similar to an ordinary pair of pliers or clippers. Formed in first and second halves 202 and 204 is central recess 216, in which is disposed barrel 218. Barrel 218 has the general form of a parallelepiped having closed sides and open ends. Opposite sides of barrel 218 are provided with holes through which rivets 214 extend, thereby securing barrel 218 to the rest of exciser 200. Extending through the open ends of barrel 218 are integral tweezers or forceps 220 comprising first and second flexible arms 222 and 224. Arms 222 and 224 are fixed together at attached end 226 of tweezers 220. Fixed to attached end 226 are short rods 228 which are separated from and attached to each other through neck 230. Rods 228 extend in directions parallel to the longitudinal axes of rivets 214.

Neck 230 extends through slot 232 centrally provided in elongate spring steel strip 234, the opposite ends 236 of which are pivotally attached to first and second exciser halves 202 and 204. Spring steel strip is plastically deformed at its center, and retains and controls longitudinal movement of integral tweezers or forceps 220 through the engagement of rods 228 with the portions of strip 234 on opposite sides of slot 232.

First and second arms 222 and 224 of tweezers 220 are provided with plastically deformed portions 238 which, when tweezers 220 are longitudinally moved in the direction of arrow 252, causes the opposed free ends 240 of first and second arms 222 and 224 to move towards each other and close. As discussed further hereinbelow, the closing action of free ends 240 of integral tweezers or forceps 220 capture the lesion to be excised, and longitudinal movement of tweezers 220 in the direction of arrow 252 pulls the lesion to be excised away from the skin.

Jaw portions 210 and 212 are each provided with opposed blades or cutting edges 242 which, when the jaws are closed, move towards each other and, when the jaws are fully closed, abut each other. Thus, skin located outside perimeter P of lesion L to be excised is pinched between blades 242 and cut from the remainder of the skin thereby. Blades 242, jaw portions 210, 212, halves 202, 204 or indeed entire exciser 200 may be made of surgical stainless steel.

Near the free ends of jaw portions 210 and 212 are located opposed, staple-engaging portions having flat surfaces 244 to which are adhered first and second separate staple halves 246 and 248 which comprise staple 250, another embodiment of a skin-closure device in accordance with the present invention. When staple halves 246 and 248 are separated or at least not fully engaged, staple 250 has an open condition. First and second staple halves 246 and 248 are, and thus staple 250 is, closed through manipulation of exciser 220 which interlocks the staple halves to each other. With the staple halves in this fully engaged state, the staple has a closed condition.

The operation of exciser 200 is now discussed with reference to FIGS. 24-27. In a first state shown in FIG. 24, free ends 240 of the integral tweezers or forceps capture lesion L to be excised from skin S, and the lesion is pinched therebetween as handle portions 206 and 208 are closed towards each other slightly.

Figure 25:
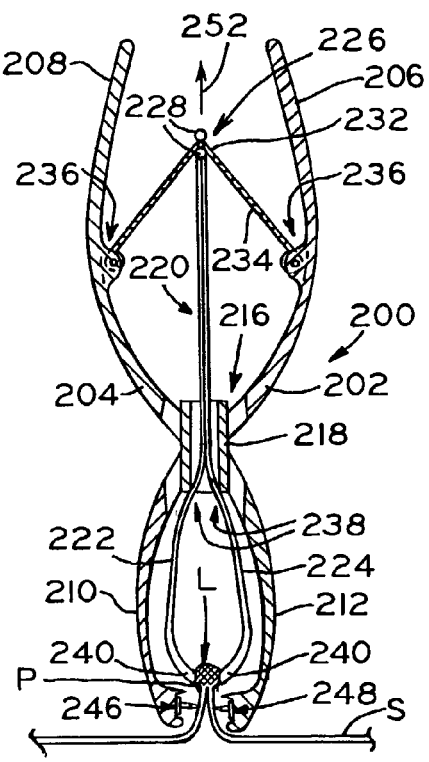
FIG. 25 shows the device of FIG. 22 in a second, sequential state, prior to lesion excision and during closure of the staple halves through the skin surrounding the lesion.

In a second, sequential state shown in FIG. 25, further movement of handle portions 206 and 208 towards each other causes spring steel strip 234 to flex and its center to move in the direction of arrow 252, which forces tweezers 220 in that direction. Movement tweezers 220 upward in the direction of arrow 252 brings deformed portions 238 of first and second arm 222 and 224 into sliding engagement with the opening of barrel 218 and forces free ends 240 of the first and second arms 222 and 224 closer together, pinching lesion L as it is pulled away from skin S. After tweezer free ends 240, and lesion L therebetween, have moved to a position within the jaws formed by portions 210 and 212 such that lesion perimeter P is past blades 242, staple halves 246 and 248 enter engagement with the skin outside of perimeter P and with each other in the manner disclosed further hereinbelow.

Figure 26:
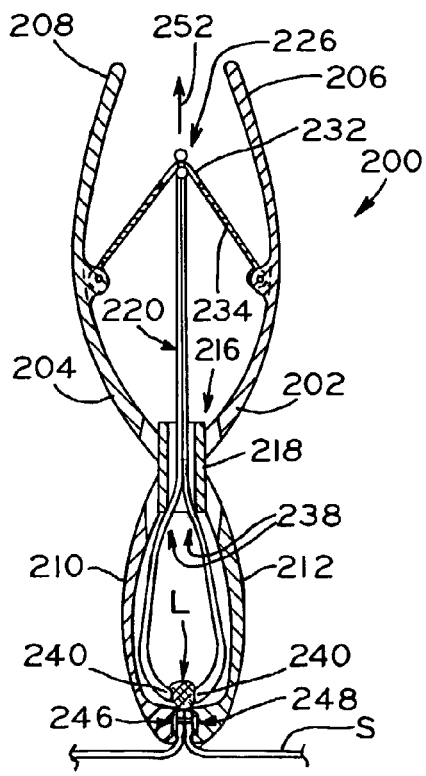
FIG. 26 shows the device of FIG. 22 in a third, sequential state, subsequent to closure of the staple and during lesion excision.

In a third sequential state shown in FIG. 26, handle portions 206 and 208 have been brought further together, and tweezers have moved further in the direction of arrow 252. In this state, staple 250 is fully closed, and blades 242 are brought into abutting engagement with each other, severing lesion L from skin S below lesion perimeter P. Although staple 250 may achieve its fully closed condition prior to actual engagement of blades 242 with skin S, the closing of the staple and the excision of lesion L may alternatively occur substantially simultaneously.

Figure 27:
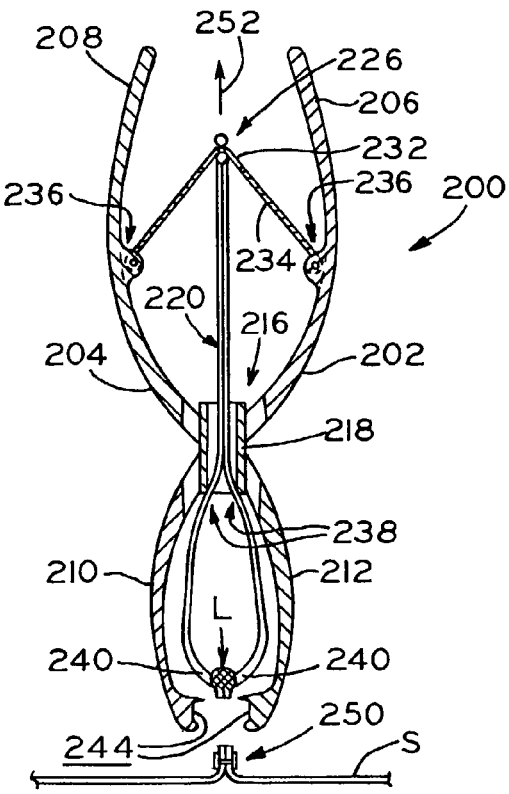
FIG. 27 shows the device of FIG. 22 in a fourth, sequential state, subsequent to lesion excision and during removal of the excised lesion from the skin.
Figure 28:
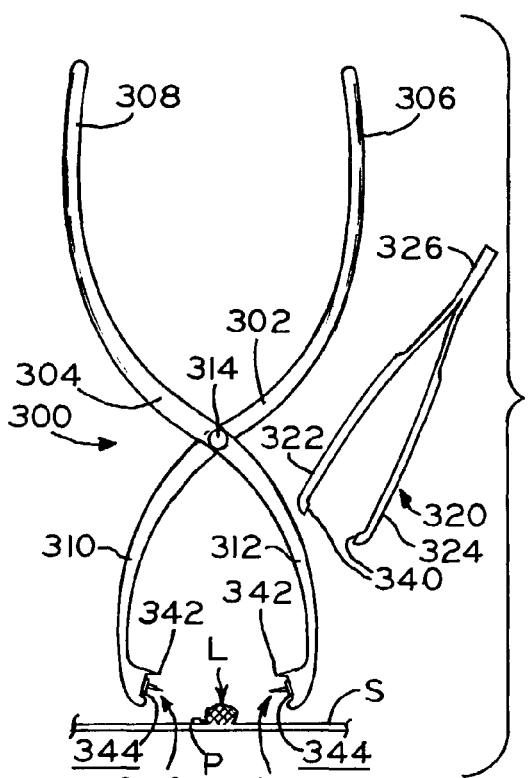
FIG. 28 is a side view of a fourth embodiment of the inventive device in a fully opened state, with separate, known tweezers or forceps also shown.

In a fourth sequential state shown in FIG. 27, exciser 200, with excised lesion L still captured between tweezer free ends 240, is removed from the patient, staple 250 having closed skin S below the excision site such that the dermis located on opposite sides of the excision site are in abutting contact and an elliptically-shaped closure wound is formed as described above. The adhesive, which holds staple halves 246 and 248 to their respective flat surfaces 244 of the staple-engaging portions at the free ends of the exciser jaws, breaks free upon slight release of handle portions 206, 208 which are urged away from each other by spring steel strip 232, and exciser 200 can then be freely removed, leaving staple 250 behind. As handle portions 206, 208 are more fully released, tweezers 220 move in a direction opposite to arrow 252, allowing free ends 240 to separate, freeing excised lesion L.

Referring now to FIGS. 28-31 there is shown exciser 300, a fourth embodiment of a device according to the present invention, in a series of sequential states of operation. Exciser 300, like exciser 200 has a basic structure similar to that of an ordinary pair of pliers or clippers, and a common skin-closure device may be used with these exciser embodiments.

Exciser 300 has a pair of elongate first and second halves 302 and 304, each respectively having handle portion 306, 308 and jaw portion 310, 312, halves 302 and 304 being pivotally joined together by pin 314. Rather than being provided with integral tweezers or forceps, as exciser 200 is, exciser 300 is used with separate, known tweezers or forceps 320 as shown. Tweezers 320 are used to capture and pull lesion L away from the skin S of the patient prior to moving handle portions 306 and 308 towards each other to close the skin-closure device or staple, and excise lesion L. Alternatively, the lesion may be captured and pulled with a skin hook (not shown). Except for these differences, the structure and operation of exciser 300 are substantially identical to those of exciser 200.

Figure 29:
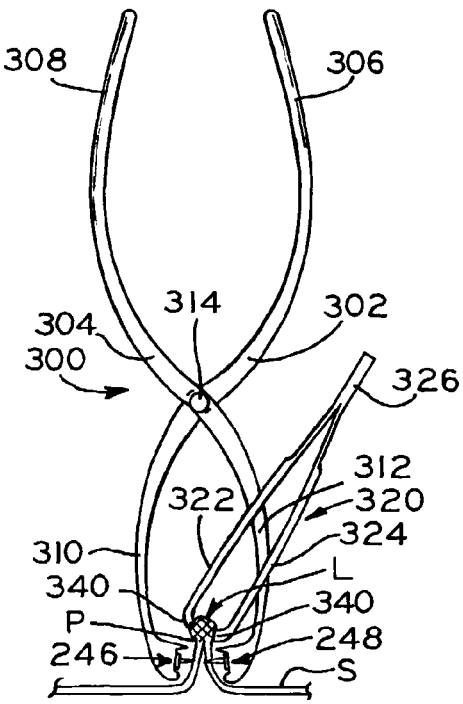
FIG. 29 shows the separate tweezers pulling the lesion away from the skin and the device of FIG. 28 in a second, sequential state, prior to lesion excision and during closure of the staple halves through the skin surrounding the lesion.

Exemplary tweezers 320 have first and second arms 322 and 324 joined at attached end 326. With the ends of jaw portions 310, 312 placed against skin S and lesion L placed loosely therebetween, tweezer free ends 340, which may be serrated, grasp lesion L which is then pulled away from skin S of the patient and into the jaws of exciser 300. Once the captured lesion has been pulled into jaw portions 310 and 312 to an extent that lesion perimeter P is above blades 342, handle portions 306 and 308 are squeezed further together, and staple halves 246 and 248 which comprise staple 250 are brought into engagement with the skin outside the outer perimeter of the lesion L and with each other, as shown in FIG. 29.

Figure 30:
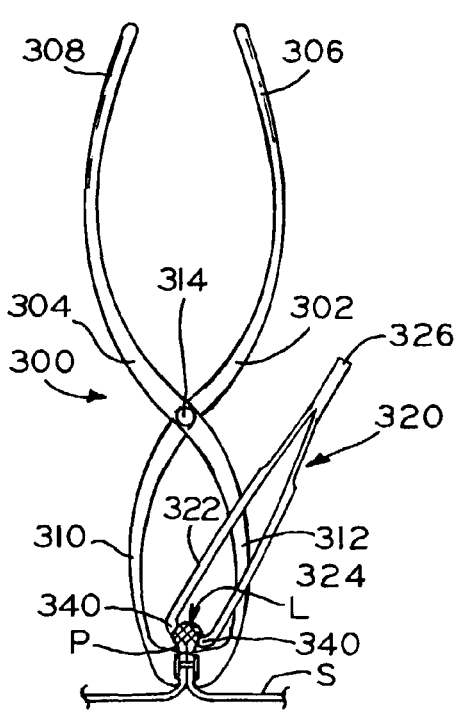
FIG. 30 shows the device of FIG. 28 in a third, sequential state, after closure of the staple and during lesion excision.
Figure 31:
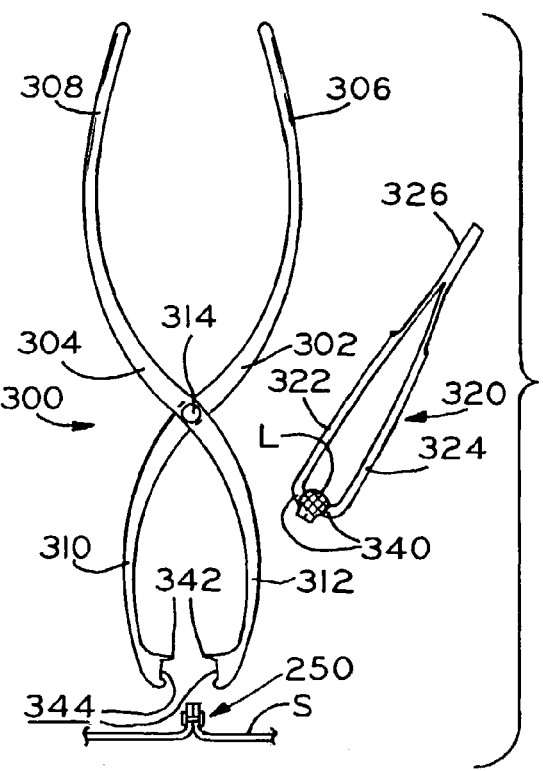
FIG. 31 shows the device of FIG. 28 in a fourth, sequential state, subsequent to lesion excision and during removal of the excised lesion from the skin with the tweezers.

In FIG. 30, staple 250 is fully closed on skin S and blades 342 sever lesion L from skin S at a location outside lesion perimeter P, as described above. As noted above, although staple 250 may achieve its fully closed condition prior to actual engagement of blades 342 with skin S, the closing of the staple and the excision of lesion L may alternatively occur substantially simultaneously. The lesion held by tweezers 320 is then removed from the excision site. In FIG. 31, the jaws of exciser 300 are separated, causing the adhesive, which held staple halves 246, 248 to flat surfaces 344 of the staple-engaging portions of the jaws, to break free. The resulting elliptically-shaped excision wound, in which the dermis located on opposite sides of the excision is held in abutting contact by staple 250, is substantially identical to that resulting from use of exciser 200.

Figure 32:
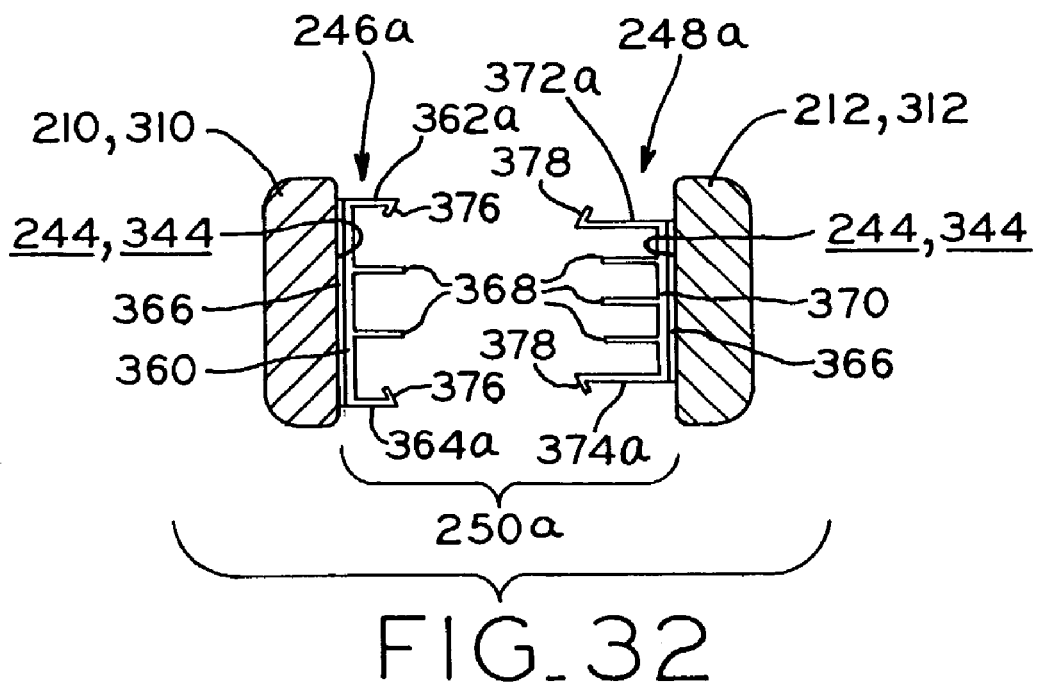
FIG. 32 is a disassembled view of a first embodiment of a two-piece staple for use with the inventive device of FIG. 22 or 28, the staple pieces shown attached thereto.
Figure 33:
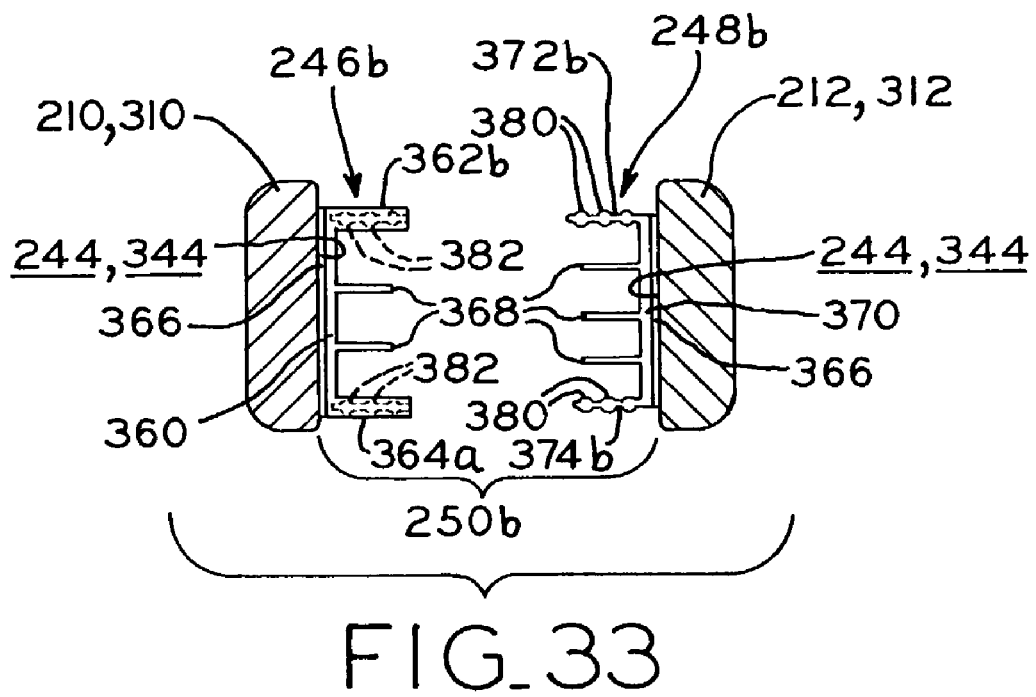
FIG. 33 is a disassembled view of a second embodiment of a two-piece staple for use with the inventive device of FIG. 22 or 28, the staple pieces shown attached thereto.

Referring now to FIGS. 32 and 33, there are respectively shown staples 250a and 250b, first and second embodiments of staple 250 which can be used with either of above-described excisers 200 and 300. Identical elements of staples 250a and 250b are identified with a common reference numeral, whereas corresponding elements of staples 250a and 250b are identified alphanumerically with a common numeric portion an alphabetic character (a or b) which correlates with a particular embodiment staple 250a or 250b. Each embodiment of staple 250 comprises staple halves 246 and 248 which, in the figure, are respectively shown adhered to flat surfaces 244, 344 of jaw portions 210, 310 and 212, 312 of excisers 200, 300. Those skilled in the art will recognize that this association between staple halves and jaw flat surfaces may be reversed. Staple halves 246, 248 may be made of surgical stainless steel or a suitable plastic material.

Each staple half 246 is provided with elongate flat central portion 360 extending between legs 362 and 364. A suitable releasable adhesive 366, which is later broken free during removal of the exciser from the patient as described above, is provided between the outer planar surface of flat central portion 360 and the abutting surface 244, 344 of jaw portion 210, 310.

Similarly, each staple half 248 is provided with elongate flat central portion 370 extending between legs 372 and 374, staple half 248 being releasably adhered to its mating jaw surface 244, 344 by adhesive 366.

Pointed pins 368 extend from the inner planar sides of flat central portions 360, 370, and when staple 250 is closed, the terminal ends of pins 368 of one staple half abut the interfacing inner surface of the other staple half. Further, with staple 250 closed, the pins alternate along the staple length on the basis of which staple half they extend from. Moreover, each staple half 246, 248 is substantially symmetrical about the center of its central portion 360, 370, thereby allowing the staple halves to each be oriented on flat surfaces 244, 344 in either of two orientations 180 degrees apart; i.e., the locations of legs 362 and 364 of staple half 246, or the locations of legs 372 and 374 of staple half 248 may be switched relative to the exciser.

Referring to FIG. 32, the ends of legs 362a and 364a are provided with barbs 376 which, when staple 250a is closed, are interconnected with barbs 378 provided at the ends of legs 372a and 374a, the interconnecting barbs holding staple 250a in its closed condition. The interconnection of barbs 376 and 378 occurs as they slide past each other, resiliently deflecting at least one leg of each interconnecting pair, and become hooked to each other.

Referring to FIG. 33, the legs 362b and 364b are substantially tubular and telescopically engage legs 372b and 374b, which are interference fitted therein during closure of staple 250b to maintain its closed condition. The engaging surfaces of legs 362b, 364b and 372b, 374b may be smooth, their sliding interference fit being substantially as disclosed above with respect to rod portions 128 and tube portions 130 of staple 122 of second embodiment exciser 100 (see FIG. 15).

Staple halves 246b, 248b which are made of plastic may alternatively have its legs 372b, 374b provided with ribs 380, as shown in FIG. 33, which are compressed as they are forced into smooth-walled hollow legs 362b, 364b, the compression of ribs 380 providing a secure interference fit between the interconnected legs. As shown in FIG. 33, the interior surfaces of hollow legs 362b and 364b may be also provided with recesses 382 into which ribs 380 are received as legs 372b, 374b are forced therein, the interfitting engagement of ribs 380 and recesses 382 holding staple 250b in its closed condition.

While the present invention has been described as having exemplary structures and methods, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for excising a removable skin portion from a surrounding skin area, the surrounding skin area defining a generally planar skin surface in which the removable skin portion initially lies, the apparatus comprising:
   a moving blade for selectively severing the removable skin portion from the surrounding skin area, the blade being movable in a blade motion plane;
   a housing supporting and at least partially enclosing the moving blade, the housing being adapted for at least partial contact with the surrounding skin area while the blade is severing the removable skin portion; and
   a closure member for closing the surrounding skin area from which the removable skin portion is excised, the closure member being actuable for movement substantially within a closure plane, wherein actuation of the closure member occurs at a predetermined time which is at least one of during and after excision of the removable skin portion;
   wherein the blade motion plane and the closure plane are positioned to extend substantially parallel to the skin surface.

2. The apparatus of claim 1, wherein at least one of the housing and the closure member includes an aperture adapted to frame the removable skin portion.

3. The apparatus of claim 1, including a driver mechanism operatively coupled to the moving blade, the driver mechanism being supported by the housing and causing movement of the blade and actuation of the closure member.

4. The apparatus of claim 1, including at least a one of tweezers and forceps adapted to selectively grasp the removable skin portion before excision, the tweezers and forceps being operative to urge the removable skin portion away from the surrounding skin area before the excision to facilitate separation of the removable skin portion and the surrounding skin area by the blade motion plane, and the tweezers and forceps being operative to remove the removable skin portion from a patient's body after the excision.

\* \* \* \* \*